(12) United States Patent
Wang et al.

(10) Patent No.: US 7,432,300 B2
(45) Date of Patent: Oct. 7, 2008

(54) GOSSYPOL CO-CRYSTALS AND THE USE THEREOF

(75) Inventors: Shaomeng Wang, Saline, MI (US); Jiangyong Chen, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 11/818,766

(22) Filed: Jun. 15, 2007

(65) Prior Publication Data

US 2007/0293585 A1 Dec. 20, 2007

Related U.S. Application Data

(62) Division of application No. 11/089,096, filed on Mar. 24, 2005, now Pat. No. 7,342,046.

(60) Provisional application No. 60/556,249, filed on Mar. 25, 2004.

(51) Int. Cl.
*A61K 31/225* (2006.01)
*A61K 31/11* (2006.01)
*A61K 31/70* (2006.01)

(52) U.S. Cl. ............... 514/569; 514/548; 514/682; 514/700; 514/25

(58) Field of Classification Search ........... 514/548, 514/569, 682, 700, 25
See application file for complete search history.

(56) References Cited

U.S. PATENT DOCUMENTS

| | | | |
|---|---|---|---|
| 3,347,885 A | 10/1967 | Jones et al. | 260/412.4 |
| 3,364,242 A | 1/1968 | Johnson et al. | 260/420 |
| 4,297,341 A | 10/1981 | Waller et al. | 424/80 |
| 4,747,979 A | 5/1988 | Gimber et al. | 260/412.4 |
| 4,806,568 A | 2/1989 | Vander Jagt et al. | 514/522 |
| 5,026,726 A | 6/1991 | Jagt et al. | 514/468 |
| 5,059,717 A | 10/1991 | Ibragimov et al. | 568/438 |
| 5,077,441 A | 12/1991 | Kuk et al. | 568/761 |
| 5,112,637 A | 5/1992 | Hron, Sr. et al. | 426/629 |
| 5,260,327 A | 11/1993 | Kim et al. | 514/405 |
| 5,277,909 A | 1/1994 | Schmidt et al. | 424/195.1 |
| 5,385,936 A | 1/1995 | Flack et al. | 514/548 |
| 5,759,837 A | 6/1998 | Kahajda et al. | 435/193 |
| 5,780,675 A | 7/1998 | Royer et al. | 562/467 |
| 6,113,397 A | 9/2000 | Flack et al. | 514/682 |
| 6,114,397 A | 9/2000 | Flack et al. | |
| 6,576,660 B1 | 6/2003 | Liao et al. | 514/456 |
| 6,608,107 B2 | 8/2003 | Wong et al. | 514/548 |
| 6,696,484 B2 | 2/2004 | Liao et al. | |
| 2002/0137801 A1 | 9/2002 | Wong et al. | |
| 2003/0008924 A1 | 1/2003 | Wang et al. | |
| 2003/0082101 A1 | 5/2003 | Taylor et al. | |
| 2003/0119894 A1 | 6/2003 | Murthy et al. | |
| 2005/0027000 A1 | 2/2005 | Reed et al. | |

FOREIGN PATENT DOCUMENTS

| | | |
|---|---|---|
| CH | 87105990 | 12/1876 |
| CH | 1033795 A | 7/1988 |
| CH | 676360 A5 | 12/1988 |
| CH | 1044455 A | 8/1990 |
| CH | 1094392 A | 11/1994 |
| CN | 87105990 | 12/1987 |
| CN | 1033795 | 12/1989 |
| CN | 1094392 | 11/1994 |
| CN | 1406919 | 9/2001 |
| DE | 1 917 341 | 4/1969 |
| DE | 19173741 | 4/1969 |
| EP | 0 651 636 B1 | 7/1993 |
| FR | 2178204 | 3/1973 |
| JP | 01132542 | 4/1969 |
| JP | 01132542 A | 11/1987 |
| JP | 001132542 A | 11/1987 |
| RU | 2067111 | 9/1996 |
| SU | 322042 A | 7/1969 |
| SU | 212245 | 10/1973 |
| SU | 322042 | 2/1976 |
| SU | 1351915 | 6/1982 |
| SU | 1351915 A1 | 6/1982 |
| SU | 2067111 | 5/1992 |
| WO | WO 94/20497 | 9/1994 |
| WO | WO 96/04250 | 2/1996 |
| WO | WO 97/40015 | 10/1997 |
| WO | WO 02/41828 A2 | 5/2002 |

(Continued)

OTHER PUBLICATIONS

V. Amberger, et al., Cancer Res., 58:149-158 (1998).

(Continued)

*Primary Examiner*—Ardin Marschel
*Assistant Examiner*—Donna Jagoe
(74) *Attorney, Agent, or Firm*—Casimir Jones S.C.

(57) ABSTRACT

This invention relates to compositions comprising co-crystals of (−)-gossypol with a $C_{1-8}$ carboxylic acid or $C_{1-8}$ sulfonic acid which are useful as inhibitors of Bcl-2 family proteins. The invention also relates to the use of co-crystals of (−)-gossypol with a $C_{1-8}$ carboxylic acid or $C_{1-8}$ sulfonic acid for inducing apoptosis in cells and for sensitizing cells to the induction of apoptotic cell death.

10 Claims, 5 Drawing Sheets

FOREIGN PATENT DOCUMENTS

WO        WO 02/47673 A2      6/2002

OTHER PUBLICATIONS

Wick et al, (W. Wick, et al., FEBS Lett., 440:419-424 (1998).
S. Mohanam et al., Cancer Res. 53:4143-4147 (1993).
P. Pedersen, et al., Cancer Res., 53:5158?5165 (1993).
Nuria Rubio, Lab Invest, 81:725-734 (2001).
Fernández et al., Cell Death Differ., 7:350-359 (2000).
J. Reed, Nature, 387:773-776 (1997).
S. Frisch and E. Ruoslahti, Curr. Opin. Cell Biol., 9:701-706 ((1997).
D. Del Bufalo, et al., FASEB J., 11:947?953 (1997).
Razakantoanina et al. Parasitol. Res., 86:665-668 (2000).
Dao et al. Bioorg. Med. Chem., 11:2001-2006 (2003).
Deck et al. J. Med. Chem., 34:3301-3305 (1991).
Przybylski et al. J. Mol. Structure, 611(1-3):193-201 (2002).
R.E. Royer et al., J. Med. Chem., 38:2427-2432 (1995).
R.E. Royer et al., Biologically active derivativse of gossypol: synthesis and antimalarial activities of peri-acylated gossylic nitriles:, J. Med. Chem., 29:1799-1801 (1986).
C.M. Venuti, J. Org. Chem., 46(15):3124-3127 (1981).
P.C. Meltzer et al., J. Org. Chem., 50(17):3121-3124 (1985).
R. Adams et al., J. Am. Chem. Soc., 60:2193-2204 (1938).
Le Blanc et al, "An in vitro study of inhibitory activity of gossypol, a cottonseed extract, in human carcinoma cell lines", Pharmacol. Res., 46:551-555 (2002).
Baumgrass et al., "Reversible inhibition of calcineurin by the polyphenolic aldehyde gossypol", J. Biol. Chem., 276:47914-47921 (2001).
Shelley et al., "Structure-activity studies on gossypol in tumor cell lines," Anticancer Drugs, 11:209-216 (2000).
Sonenberg et al., "Anti-fertility and othe ractions of gossypol analogues", Contraception, 37:247-255, (1988).
Whaley et al, ."Monkey lactate dehydrogenase-C4 as a model for the interaction of enzymes with gossypol", Contraception, 33:605-616 (1986).
Dorsett et al., "Letter: Antiviral activity of gossypol and apogossypol", J. Pharm. Sci., 64:1073-1075 (1975).
Wu et al., "Synthesis and antifertility actions of gossypol derivatives and phenol aldehydes", Yao Xue Xue Bao, 24:502-511 (1989).
Hoffer et al., "Antifertility, spermicidal and ultrastructural effects of gossypol and derivatives administered orally and by intratesticular injections", Contraception, 37:301-331 (1988).
Guo et al., "Synthesis of mono-aldehyde gossypol and its analogues", Yao Xue Xue Bao, 22:597-602 (1987).
Manmade et al., "Gossypol. Synthesis and in vitro spermicidal activity of isomeric hemigossypol derivatives", Experientia, 39:1276-1277 (1983).
Dowd, Chirality, 15:486 (2003).
Ciesielska et al., Chem. Phys. Lett. 353:69 (2002).
Vermel et al., Antitumour Activity of Gossypol in Experiments on Transplanted Tumours 39-43 (1963).
Freedman et al., Chirality, 15:196 (2003).
J.C. Reed, Pharmacology, 41:501-553 (1997).
J.C. Reed et al., J. Cell Biochem., 6:23-32 (1996).
Z. Han et al., Cancer Res., 56:621-628 (1996).
S.W. Muchmore et al., Nature, 381:335-341 (1996).
A.M. Petros et al., Protein Sci., 9:2528-2534 (2000).
A.M. Petros et al., Proc. Natl. Acad. Sci. U.S.A., 98:3012-3017 (2001).
X.M. Yin et al., Nature, 369:321-323 (1994).
S.C. Cosulich et al., Curr. Biol., 7:913-920 (1997).
A. Sali et al., Structure, Function, and Genetics, 23:318-326 (1995).
A. Sali, Curr. Opin. Biotech., 6:437-451 (1995).
J.L. Wang et al., Cancer Res., 60:1498-1502 (2000).
J.L. Wang et al., Proc. Natl. Acad. Sci. U.S.A., 97:7124-7129 (2000).
Sattler et al., Science, 275:983-986 (1997).
B.R. Brooks et al., J. Comp. Chem., 4, 187-217 (1983).
P.V.R. Schleyer et al., CHARMM: The Energy Function and Its Parameterization with an Overview of the Program, in The Encyclopedia of Computational Chemistry, 1:271-277 eds., John Wiley & Sons, Chichester (1998).
S. Makino and I.D. Kuntz, J. Comput. Chem. 18:1812-1825 (1997).
I.J. Enyedy et al., J. Med. Chem., 44:313-4324 (2001).
Leschev, "Influence of the Extract of Eleutherococus senticosus on development of experimental pituitary adenomas in rats", Institute of Oncology of the U.S.S.R. Academy of Medical Sciences, 60-67 (1966).
La Blanc et al., An in vitro study of inhibitory of gossypol, a cottonseed extract, in human carcinoma cell lines, Pharmacol. Res. 46(6):551-5 (2002).
Griffith et al., Bioenvision Successfully Completes Formulation Research to Develop Gossypol as a Novel Anti-Cancer Agent, Bioenvision News (2003).
Saydachmov et al., Uebekskii Khimicheski Zhumal (1):11-13 (1994).
Zakhidov et al., Modifying Cytogenetic Effects of Gossypol and Derivatives, Library National Institutes of Health (1994).
Yerukhimov, Treatment of Bladder Tumors With Gossipol And Ionol In Combination With Surgical Intervention, Issues in Oncology, XI (1966.
Kuznezova et al., Pharmacol. Toxicol., Boston Library Boston Spa (1979).
Zhong et al., National Library of Medicine, 2:159-161 (1982).
Zhang et al., Inhibitory effects (-)-gossypol on proliferation and keratinocyte growth factor expression in human breast epithelial cells, stromal cells, and adipocytes, American Association fro Cancer Research 38:218 (1997).
Zheng et al., Gossypol (GP) Stimulates Transforming Growth Factor Beta (TGF-â) Gene Expression in Human Breast Cancer Cell Line, The FASEB Journal 10:A757 (1996).
Zheng et al., Studies on the Resolution of Racemic Gossypol, ACTA Pharmaceutica Simica 25(6):430-434 (1990).
Adlakha et al., Inhibition of DNA Polymerase á And Ribonucleotide Reductase by By Gossypol, Proceedings of AACR 26:249:982 (1985).
Akhila et al., Biosynthesis of Gossypol in *Thespesia Populnea*, Phytochemistry 33:335-340 (1993).
Badria et al., Antimitotic Activity of Gossypol and Gossypolone, Pharmaceutical Biology, 39:120-126 (2001).
P. Baille et al., Clin. Cancer Res., 3:1535-1538 (1997).
Balci et al., Gossypol induced apoptisis in the human promyelocytic cell line HL60, Cytogenet Cell Genet 85:5-181 (1999).
Balci et al., Gossypol Induced Apoptosis in the Human Promyelocytic Leukemia Cell Line HL 60, Tohoku J. Exp. Med. 189:51-57 (1999).
Band et al., Antiproliferative Effect Of Gossypol and Its Optical Isomers on Human Reproductive Cancer Cell Lines, Gynecologenic Oncology 32:273-277 (1989).
Band et al., Cytocidal Effects of Gossypol and Its Optical Isomers on Reproductive Cancer Cell Lines, Gynecologic Oncology 23:261 (1986).
Benz et al., Lactic Dehydrogenase Isozymes, $^{31}$P Magnetic Resonance Spectroscopy, and in Vitro Antimitochondrial Tumor Toxicity with Gossypol and Rhodamine-123, J. Clin. Invest. 79:517-523 (1987).
Benz et al., Selective Toxicity of Gossypol Against Epithelial Tumors and its Detection by Magnetic Resonance Spectroscopy, Contraception 37:221-229 (1988).
Benz et al., Gossypol Enantiomers (+, −) Difference Uncouple Tumor Mitochondria, Block Glutathione-S-Transferase Acitivity, and Inhibit Cellular Proliferation, Proceedings of AACR 29:322 (1988).
Benz et al., Biochemical Correlates of the Antitumor and Antimitochondrial Properties of Gossypol Enantiomers, Molecular Pharmacology 37:840-847 (11990) (1990).
Benz et al., Gossypol Effects on Endothelial Cells and Tumor Flow, Life Sciences 49:67-72 (1991).
Blackstaffe et al., Cytotoxicity of gossypol enantiomers and its quinone metabolite gossypolone in melanoma cell lines, Melanoma Research 7:364-372 (1997).

Bourinbaiar et al., Comparative in vitro study of contraceptive agents with anti-HIV activity: *Gramicidin, nonoxynol-9, and gossypol*, Contraception 49:131-137 (1994).

Brandes et al., New Drugs in Recurrent High Grade Gliomas, Anticancer Research 20:1913-1920 (2000).

Brandes et al., New therapeutic agents in the treatment of recurrent high-grade gliomas, FORUM Trends in Experimental and Clinical Medicin 10:121-131 (2000).

R. Bruno et al., J. Clin. Oncol., 16:187-196 (1998).

Bushunow et al., Gossypol Treatment of Recurrent Adult Malignant-Gliomas, Proceedings of ASCO, 14:282 (1995).

Bushunow et al., Gossypol Treatment of recurrent adult malignant gliomas, Journal of Neuro-Oncology 43:79-86 (1999).

Chang et al., Antiproliferative and Antimetastatic Effects of Gossypol (GP) on Mat-Lylu-Bearing Rats, FASEB Journal, 6:3794 (1992).

Chang et al., Prostate, begin hypertrophy and prostatic carcinoma: A study of cell biology of prostate and chemotherapy for prostatic hypertrophy and prostatic cancer, Dissertation Abstract International, 55:4330-B (1995).

Chang et al., Potential of Gossypol (GP) and Transforming Growth Factor-â, (TGF-â$_1$) as Inhibitors of Canine Prostate Growth, FASEB Journa 9:4813-4814 (1995).

Chang et al., Antiproliferative and Antimetastatic Effects of Gossypol on Dunning Prostate Cell-Bearing Copenhagen Rats, Research Communications in Chemical Pathology and Pharmacology 79:293-312 (1993).

Chen et al., Application of 2D NMR Techniques in the Structure Determination of Ganosporelactone A and B, ACTA Pharmaceutica Simica 26:430-436 (1991).

Coyle et al., In-Vitrop and in vivo cytotoxicity of gossypol against central nervous system tumor cell lines, Journal of Neur-Oncology 19:25-35 (194) (1994).

Dallacker er al., Uber Gossypol- und Hemigossypol-Derivate—Darstellung von Hydroxy-methyl-naphto[1,3] dioxolen, Chemiker-Zeitung 113:5 11 (1989).

Dallacker et al., Darstellung von Methyl-isopropyl-naphthol-derivaten durch Pd-katalysierte Cyclocarbonylierung, Chemiker-Zeitung 114:144-147 (1990).

Dao et al., Synthesis and cytotoxicity of gossypol related compounds, Eur. J. Med. Chem. 35:805-813 (2000).

Darzynkiewicz et al., Cytometry in Cell Necrobiology: Analysis of Apoptosis and Accidental Cell Death (Necrosis), Cytometry 27:1-20 (1997).

Data et al., A Study of the Derivatives of (±)-Gossypol, Indian Journal of Chemistry 10:691-693 (1972).

Davila et al., Toxocological Studies of Gossypol in Primary Culture of Postnatal Rat Hepatocytes, Journal of Molecular and Cellular Toxicology 4:161-170 (1991).

Deck et al., Gossypol and Derivatives: A New Class of Aldose Reductase Inhibitors, J. Med. Chem. 34:3301-3305 (1991).

DeMartino et al., Electron microscopic and biochemical studies of the effect of Gossypol on Erlich ascites tumor cells, Caryologia, International Journal of Cytology, Cytosystematics and Cytogenetics 35:114-115 (1982).

de Peyster et al., Genetic toxicity studies of gossypol, Mutation Research 197;293-312 (1993).

De-yu et al., Mutagenicity of gossypol analyzed by inductio of meiotic micronuclei vitro, Mutation Research 208:69-72 (1988).

Dhaliwal et al., Cytogenetic Analysis of a Gossypol-Induced Murine Myxosarcoma, Journal of the National Cancer Institute, 78:1203-1209 (1987).

A. Degterev et al., Nat. Cell Biolog., 3:173-182 (2001).

Dogliotti et al., Cytotoxic chemotherapy for adrenocortical carcinoma, Minerva Endocrinologica, 20:105-109 91995).

Edwards et al., Sysnthesis of Gossypol and Gossypol Derivatives, Journal of the American Oil Chemists' Society 47:441-442 (1970).

Finaly et al., Mechanism of the Gossypol Inactivation of Pepsinogen, Journal of Biological Chemistry 248:4827-4833 (1973).

Fish et al., The Photo-epimerisation of Gossypol Schiff's Bases, Tetrahedron: Asymmetry 6:873-876 (1995).

Flack et al., Treatment of adrenocortical carcinoma with gossypol, Proceedings of American Asssociation for Cancer Research 31:198 (1990).

Flack et al., Oral Gossypol in the Treatment of Metastatic Adrenal Cancer, Journal of Clinical Endocrinology and Metabolism, 76:1019-1024(1993).

Floridi et al., The Effect of the Association of Gossypol and Lonidamine on the Energy Metabolism of Ehrlich Ascites Tumor Cells, Experimental and Molecular Pathology 38:322-335 (1983).

Floridi et al., The Effect of Gossypol and Lonidamine on Electron Transport in Ehrlich Ascites Tumor Mitochondria, Experimental and Molecular Pathology 40:246-261 (1984).

Ford et al., Modulatio nof resistance of alkylating agents in cancer cell by gossypol enantiomers, Cancer Letters 56:85-94 91991)(1991.

Gilbert et al., Antiproliferative Activity of Gossypola nd Gossypolone in Human Breast Cancer Cells, Life Sciences 57:61-67 (1995).

Gonzalez-Garza et al., Cytotoxic Effects of Gossypol and Vitamin E on Human and Rat Lymphocytes and Spermatozoa, Nutrition Reports International (1995).

Gorczyca et al., The Cell Cycle Related Differences in Susceptibility of HL-60 Cells to Apoptosis Induced by Various Antitumor Agents, Canc Research 53:3186-3192 (1993).

Grankvist, Gossypol-Induced Free Radical Toxicity to Isolated Islet Cells, Int. J. Biochem. 21:853-856 (1989).

Hamasaki et al., Gossypol, a potent inhibitor of arachidonate 5- and 12-lipoxygenases, Biochimica et Biophysica Acta 834:37-41 (1985).

Han et al., Gossypol in the Treatment of Endometriosis and Uterine Myoma, Chontr. Gynec. Obstet. 16:268-270 (1987).

Haroz et al., Tumor Initiating And Promoting Activity of Gossypol, Toxicology letters, 72 (1980).

Haspel et al., Cytocidal Effect of Gossypol on Cultured Murine Erythroleukemia Cells is Prevented by Serum Protein, Journal of Pharmacology and Experimental Therapeutics 229:218-225 (1984).

J. Hirth et al., Clin. Cancer Res., 6:1255-1258 (2000).

Heinstein et al., The Biosynthesis of Gossypol, Biochemistry, 28:1342-B (1967).

Hendricks et al., Hepatocarcinogenicity of Glandless Cottonseeds and Cottonseed Oil to Rainbow Trout (*Salmo gairdnerii*), Science 208:309-311 (1980).

Herve et al., Contraceptive gossypol blocks cell-to-cell communication in human and rat cells, European Journal of Pharmacology 313:243-255 (1966).

Hong et al., Study of the Effects of Acetate Gossypol, High Energy Shock Waves (HESW) and Their Combination on the Human Bladder Cancer Cell Line $BT_{5637}$, ACTA Anatomica Sinica 25:291-296- (1994).

Hu et al., Gossypol Effects on Cultured Normal and Malignant Melanocytes, In Vitro Cellular & Development Biology 22:583-588 (1986).

Hu et al., Gossypol Inhibits Basal And Estrogen ($E_2$)-Stimulated DNA Synthesis in Human Breast Carcinoma (HBC) Cells, FASEB Journal, 7:3982 (1993).

Hu et al., Gossypol Inhibits Basal And Estrogen-Stimulated DNA Synthesis in Human Breast Carcinoma Cells, Life Sciences 53:433-439 (199.

Hu et al., Presence of antitumor activities in the milk collected from gossypol-treated dairy cows, Cancer Letters 87:17-23 (1994).

Huang et al., Resolution of Racemic Gossypol, Journal of Ethnopharmacology 20:13-20 (1987).

Hutchinson et al., The mechanism of gossypol acetic acid cytotoxicity, Dissertation Abstracts International, 59:1612-B (1998).

Hutchinson et al., Attenuation of Gossypol Cytotoxicity by Cyclic AMP in a Rat Liver Cell Line, Toxicology and Applied Pharmacology 151:311-318 (1998).

Jaroszewski et al., Action of Gossypol and Rhodamine 123 on Wild type and Multidrug-resistant MCF-7 Human Breast Cancer Cells: $^{31}P$ Nuclear Magnetic Resonance and Toxicity Studies, Cancer Research 50:6936-6943 (1990).

Jarvis et al., INduction of Apoptotic DNA Fragmentation and Cell Death in HL-60 Human Promyelocytic Leukemia Cells by Pharmacological Inhibitors of Protein Kinase C[1], Cancer Research 54:1707-1714 (1994).

Jiang et al., The Effects of Gossypol on the Invasiveness of MAT-LyLu Cells and MAT-LyLu Cells from the Metastasized Lungs of MAT-LyLu-Bearing Copenhagen Rats, Anticancer Research 20:4591-4598 (2000).

Jia-xin et al., Studies on the Synthesis of Gossypol Derivatives and Their Antifertility Action, Reproduction and Contraception 6:48:51 (1986).

Joingfang et al., Of Gossypol in Mice, Rats and Human Tumor Cell Lines and Its Possible Mechanism, ACTA Academiae Medicinae Sinicase 8:486-488 (1986).

Jolad et al., Tumor-Inhibitory Agent from *Montezuma speciosissima* (Malvaceae), Journal of Pharmaceutical Sciences 64:1889-1890 (1975).

Joseph et al., Cytotoxicity of enantiomers of gossypol, Br. J. Cancer 54:511-513 (1986).

Jung et al., Recent Studies on Natural Products as Anti-HIV Agents, Current Medicinal Chemistry 7:649-651 (2000).

Kai et al., Resolution of Racemic Gossypol, J. Chem. Soc., Chem. Commun. 3:168:169 (1985).

Kaplan et al., Metabolism of breast cancer cells as revealed by non-invasive magnetic resonance spectroscopy studies, Breast Cancer Research and Treatment 31:285-299 (1994).

Keller et al., Novel pharmacophore-based methods reveal gossypol as a reverse transcriptase inhibitor, Journal of Molecular Graphics and Modelling 5346:1-9 92002). (2002).

Keniry et al., Magnetic Resonance Spectroscopy (MRS) and Imaging (MRI) in the Evaluation of Tumor Growth and Chemotherapy Response, Proceedings of AACR 27:384 (1986).

Keniry et al., The Effect of Gossypola nd 6-Aminonicotinamide on Tumor Cell Metabolism: A $^{31}$P-Magnetic Resonance Spectroscopic Study, Biochemical and Biophysical Research Communications 164:947-953 (1989).

Kim et al., Comparative In Vitro Spermicidal Effects of (±)-Gossypol, (+)-Gossypol, (−)-Gossypolone, Contraception 30:253-259 (1984).

Latronico et al., Extensive Personal Experience Adrenocortical Tumors, Journal of Clinical Endocrinology and Metabolism 82:1317-1324 (1997).

LaVoie et al., Investigation of Intracellular Signals Mediating The Anti-Apoptotic Action of Prolactin in Nb2 Lymphoma Cells, Society for Experimental Biology and Medicine 257-269 (1995).

Lee, Novel Antitumor Agents from Higher Plants, Medical Research Reviews, 19:569-596 (1999).

Lee et al., Plant PHenolic Compounds as Cytotoxic Antitumor Agents, American Chemical, Society 29:367-379 (1992).

Lefeng et al., Clinical Effects and Experimental Study on Gossypol in Endometriosis, Chin. J. Integr Med. 9(8):451-464 (1989).

Levine, Inhibition of the A-23187-Stimulated Leukotriene And Prostaglandin Biosynthesis of Rat Basophil Leukemia (RBL-1) Cells By Non-Steroidal Anti-Inflammatory Drugs, Anti-Oxidants, and Calcium Channel Blockers, Biochemical Pharmacology 32:3023-3025 (1983).

Li et al., DNA-Breaking Versus DNA-Protecting Activity of Four Phenolic Compounds in vitro, Free Rad. Res. 33:551-566 (2000).

Llian et al., Hepatoma Initiating and Promoting Effects of Gossypol, ACTA Academic Medicinae Sinicase (1985).

Liang et al., Developing gossypol derivatives with enhanced antitumor activity, Investigational New Drugs 13:181-186 (1995).

Liqueros et al., The antiproliferative Effects of Gossypol and the Retinoblastoma Gene Protein, Clinical Pharmacology & therapeutics 57:206 (1995).

Liqueros et al., Gossypol inhibition of mitosis, cyclin D1 and Rb protein in human mammary cancer cells and cyclin-D1 transfected human fibrosarcoma cells, British Journal of Cancer 76:(1):21-28 (1997).

Lin et al., Selective Inhibition of Human Immunodeficiency Virus Type 1 Replication by the (−) but Not the (+) Enantiomer of Gossypol, Antimicrobial Agents and Chemotherapy, 2149-2151 (1989).

Lin et al., Anti-HIV-1 Activity and Cellular Pharmacology of Various Analogy of Gossypol, Biochemical Pharmacology 46:251-255 (1993).

Lin et al., Gossypol and tamoxifen prevent estrogen-induced renal carcinogenesis in hamsters, Proceedings of the American Association for Cancer Research 36:391-2329 (1995).

Majumdar et al., Genotoxic Effects of Gossypol Acetic Acid on Cultured Murine Erythroleukemia Cells, Environment and Molecular Mutagenesis 18:212-219 (1991).

Matlin et al., Large-Scale Resolution of Gossypol Enantiomers for Biological Evaluation, Contraception 37:229-237 (1998).

McSheehy et al., Gossypol, a cytoxic agent, may uncouple respiration of Ehrlich ascites tumor cells, Biochemical Society Transactions 16:616-617 (1988).

Meiling, Gossypol Treatment for Menopausal Functional Bleeding, Myoma of Uterus and Endometriosis—Preliminary Report, ACTA Academi Medicinae Sinicae 2:167-169 (1980).

Meltzer et al., A Regioselective Route to Gossypol Analogues: The Synthesis of Gossypol and 5,5'- Didesisopropyl-5,5'-diethylgossypol, J. Org Chem. 50:3121-3124 (1985).

Fujii et al., "Effect of cerulenin, an inhibitor of fatty acid synthesis, on the immune cytolysis of tumor cells" Jpn. J. Exp. Med Jun. 1986;56(3):99-106 (Abstract only).

Gossypol, Xian Oil 7 Fat Works, Drugs of the Future, vol. 21, No. 5, 1996.

Meyers et al., The synthesis of (S)-(+)-gossypol via an asymmetric Ullmann coupling, Chem. Commun. 1573-1584 (1997).

Moh et al.., Effect of Gossypol (GP) on a 5á-Reductase and a 3á-Hydroxysteroid Dehydrogenase (3á-HSD) in Adult Rat Testes, FASEB Journ 6342 (1992.

Mohan, Problems and Perspectives in the Design of Anti-HIV-1 Agents, Drug Development Research 29:1-17 (1993).

S.W. Muchmore et al., Nature, 381:335-341 (1996)). , and.

Mushtaq et al., Gossypol (GP) Inhibits in Vitro Porcine Oocyte Maturation and Early Embryonic Development in Modified Simple Media, Society for the Study of Reproduction, 52:172 (1998).

Naik et al., Preclinical studies of gossypol in prostate carcinoma, International Journal of Oncology 6:209-213 (1995).

Nayak et al., Induction of Sister Chromatid Exchanges and Chromosome Damage by Gossypol in Bone Marrow Cells of Mice, Teratogenesis, Carcinogenesis, and Mutagenesis 6:83-91 (1986).

Newman et al., Pharmacokinetics and toxicity of 120-hour continuous-infusion hydroxyurea in patients with advanced solid tumors, Cancer Chermother Pharmacol 39:254-258 (1997).

Ng et al., Anti-Human Immunodeficiency virus (Anti-HIV) Natural Products with Special Emphasis on HIV Reverse Transcriptase Inhibitors. Life Sciences 61:933-949 (1997).

Ognyanov et al., Synthesis of Gossypol Analogues, Helvetica Chimica ACTA 72:353-360 (1989).

Ohuchi et al., Inhibition of gossypol of tumor promoter-induced arachidonic acid metabolism in rat peritoneal macrophages, Biochimica et Biophysica Acta, 971:85-91 (1988).

Olgiati et al., Gossypol Inhibition of Adenylate Cyclase, Archives of Biochemistry and Biophysics 231:411-415 (1984).

Papageorgiou et al., A New Method for the Isolation of Gossypol From Cottonseed-Oil Fatty Acids, Chimika Chronika 7:101-109 (1978).

Perez et al., Studies on spermatogenesis and apoptosis in the bovine, Disseration Abstracts International 50:526-B (1999).

Phung et al., Isolation and Purification of Gossypol in Cotton Seeds of Vietnam, Tap chi Hoa hov, 35:91-93 (1997).

Pirogov et al., Postoperative Bronchopleural Complications in Combined Treatment of Pulmonary Cancer, Issues of Oncology, 20:24-28 (1974.

Polsky et al., Inactivation of Human Immunodeficiency Virus (RIV) By Gossypol (GP), Clinical Research 35(3)487A (1987).

Polsky et al., Inactivation of Human Immunodeficiency Virus in Vitro by Gossypol, Contraception, 39:579-587 (1989).

Przybylski et al., Spectroscopic studies and PM5 semiempirical calculations of new Schiff bases of gossypol with amino derivates of crown ethers, Journal of Molecular Structure, 16:04-1-9 (2002).

Oian, Gossypol: A Potential Antifertility Agent for Males, Ann. Rev. Pharmacol. Toxicol. 24:329-60 (1984).

Qui et al., The Search for Gene(s) Conferring Sensitivity to Cell Killing by Gossypol, The FASEB Journal 13:A151A (1999).

J. O'Quigley et al., Biometrics 46:33-48 (1990).

Quintana et al., Gossypol-induced DNA breaks in rat lymphocytes are secondary to cytotoxicity, Toxicology Letters 117:85-94 (2000).

Rao et al., Antitumor effects of gossypol on murine tumors, Cancer Chemother Pharmacol. 15:20-25 (1985).

Razakantoanina et al., Antimalarial activity of new gossypol derivatives, Parasitol Res. 86:665-668 (2000).

Rekha et al., Inhibition of Human Class 3 Aldehyde Dehydrogenase, and Sensitization of Tumor Cells that Express Significant Amounts of thi Enzyme to Oxazaphosphorines, by the Naturally Occuring Compounds Gossypol, Enzymology and Molecular Biology of Carbonyl Metabolis 6, 133-146 (1996).

Resnick et al., Comparitive Evaluation of Sperimicidal Agents with Virucidal Activity Against HIV, IXth International Conference on AIDS, 11:PO-C22-3154 (1993).

Rosenberg et al., Biochemical Basis for the Gossypol-indiced Inhibition of DNA Replication in Mammalian Cells, American Association for Cancer Research, 29:1291 (1988).

Royer et al., Inhibition of Human Immunodeficiency Virus Type 1 Replication by Derivatives of Gossypol, Pharmacological Research, 24:407-412 (1991).

G. Rassidakis et al., Amer. J. Path., 159:527-535 (2001).

J.C. Reed et al., Ann. Oncol., 5:61-65 (1994).

Sampath et al., A Rapid Procedure for the Resolution of Racemic Gossypol, J. Chem. Soc., Chem. Commun., 649-650 (1986).

Schinazi et al., Insights Into HIV Chemotherapy, Aids Research and Human Retroviruses, 8:963-990 (1992).

A.F. Schott et al., Oncogene, 11:1389-1394 (1995).

Seidman et al., Gossypol in Advanced Breast Cancer, Journal of Investigative Medicine 46:213A (1998).

Seidman, Chemotherapy for Advanced Breast Cancer: A Current Perspective, Seminars in Oncology, 23:55-59 (1996).

Shelly et al., Stereo-specific cytotoxic effects of gossypol enantiomers and gossypolone in tumor cells lines, Cancer Letters, 135:171-180 (1999).

Shelly et al., Structure-activity studies on gossypol in tumor cell lines, Anti-Cancer Drugs, 11:209-216 (2000).

S. Shi et al., J. Histochem. Cytochem., 39:741-748 (1991).

Shidaifat et al., Differential regulation of gene expression by gossypo0l: A potential inhibitor of prostate cell growth, Dissertation Abstracts International, 57:6097-B(1997).

Shidaifat et al., Inhibition of human prostate prostate cancer cells growth by gossypol is associated with stimulation of transforming growth factor-ä, Cancer Lettesr 107:37-44 (1996).

Shidaifa et al., Gossypol Arrests Human Benign Prostatic Hyperplasia Cell Growth at G0/G1 Phase of the Cell Cycle, Anticancer Research 17:1003-1010 (1997).

Sinnhuber et al., Dietary Factors and Hepatoma in Rainbow Trout (*Salmo gairdneri*). II. Cocarcinogenesis by Cyclopropenoid Fatty Acids and the Effect of Gossypol and Altered Lipids on Aflatoxin-Induced Liver Cancer, Journal of the National Cancer Institute, 41:1293-1299 (1968).

Stein et al., A preliminary clinical study of gossypol in advanced human cancer, Cancer Chemother Pharmacol 30:480-481 (1992).

Sugimoto et al., Differential proliferative responses to the (-)-enantiomer of gossypol in cultured human breat epithelial and stromal cells, American Association for Cancer Research 40:4 (1999).

Tai, Rat Basophilic Leukemia-1 Cell Processes 12-Lipoxygenase and 5-Lipoxygenase activities which are specifically inhibited by gossypol acetic acid, Japanese Journal of Allergology 33:1040-1046 (1984).

Tan et al., Evaluation of Natural Products As Inhibitors of Human Immunodeficiency Virus Type 1 (HIV-1) Reverse Transcriptase[1], Jouranl of Natural Products, 54:143-154 (1991).

Tanphaichitr et al., Direct Effect of Gossypol on TR-ST Cells: Perturbation of Rhodamine 123 Accumulation in Mitochondria, Biology of Reproduction, 31:1049-1060 (1984).

Tao et al., The Effects of Gossypol on Human BPH Cells In Vitro, 21:31 (1994).

Teng et al., c-Myc Protein Expression in spermatocytes During Gossylpol-Induced Apoptosis, Molecular Biology of the Cell, 364a:2116 (199.

Teng et al., Biphasic c-MYC Protein Expression During Gossypol-Induced Apoptosis in Rat Spermatocytes, Contraception 57:117-123 (1998).

Teng, C-Fos Protein Expression in Apoptoic Rat Spermatocytes Induced by Gossypol, Contraception 57:281-286 (1998).

Thoenes et al., Cytotoxic Effects of Adriamycin, Bleomycin, Gossupol and Hydroxyanisol to Cultured Human Malignant Melanoma Cells, Journal of Cancer Research and Clinical Onocology, 113:D-THER:12, S46 (1987).

Thomas et al., Effects of Gossypol on the Cell Cycle Phases in T-47D Human Breat Cancer Cells, Anticancer Research 11:1469-1476 (1991).

D.K. Trask et al., Laryngoscope, 112:638-644 (2002).

Troll et al., Free Oxygen Radicals: Necessary Contributors to Tumor Promotion and Cocarcinogenesis, Proceedings of the 14th International Symposium of The Princess Takamatsu Cancer Research Fund, 207-218 (1984).

Tso, Gossypol Inhibits Ehrlich Ascites Tumor Cell Proliferation, Cancer Letters 24:257-261 (1984).

Tuszynski et al., Differential Cytotoxic Effect of Gossypol on Human Melanoma, Colon Carcinoma, and Other Tissue Culture Cell Lines, Cancer Research 44:768-771 (1984).

Vander Jagt et al., Gossypol: Prototype of Inhibitors Targeted to Dinucleotide Folds, Current Medicinal Chemistry 7:479-498 (2000).

Van Poznak C. et al., Oral Gossypol in the treatment of patients with refractory metastatic breast cancer: A phase I/II clinical trial, Breat Cancer Research and Treatment 66:239-248 (2001).

Vlietinck et al., Plant-Derived Leading Compounds for Chemotherapy of Human Immunodefiency Virus (HIV) Injection, PlantaMedica 64:9 109(1998).

Wang et al., Effect of Gossypol on DNA Synthesis and Cell Cycle Progression of Mammalian Cells in Vitro, Cancer Research 44:35-38 (1984).

Wang et al., Cytotoxic effect of gossypol on olonn carcinoma cells, Life Sciences 67:2663-2671 (2000).

P. Watkins, Pharmacogenetics, 4:171-184 (1994).

Wichmann et al., Inhibiting herpes simplex virus 2 infection in human epithelial cells by gossypol, a potent spermicidal and contraceptiv agent, Am. J. Obstet. Gynecol. 142:593-594 (1982).

Wu et al., Pharmacokinetics of (±)-, and (+)-, and (−)-gossypol in humans and dogs, Clinical Pharmacology & Therapeutics 39:613-618 (1996).

Wu et al., An in Vitro and in Vivo Study of Antitumor Effects of Gossypol on Human SW-13 Andrenocortical Carcinoma, Cancer Research 49:3743-3758 (1989).

Wu et al., In vitro antitumor activity of gossypol alone or in combination with amsacrine, European Journal of Pharmacology 183:230 (1990).

Xuequing et al., Clinical Observation and Experimental Study of Gossypol in Treatment of Dysfunctional Menorrhagia, Endometriosis and Fibromyoma of Uterus, Chinese Journal of Integrated Traditional and Western Medicine8:197 (1999).

Ye et al., The Modulation of Gap Junctional Communication by Gossypol in Various Mammalian Cell Lines in Vitro. Fundamental And Appli Toxicology 14:817-832 (1990).

Ye et al., Toxicity of a Male Contraceptive, Gossypol, in Mammalian Cell Cultures, In Vitro 19:53-57 (1983).

Yikang et al., Studies on Resolution of Racemic Gossypol, Sinica 30:297-303 (1987).

Ying et al., Studies on Frequencies of Sister Chromatid Exchange in Peripheral Blood Lymphocytes Before and After Gossypol Treatment, Pro DAMS and PUMC 1:34-36 (1986).

Youfang et al., Ultrastructural Changes of Smooth Muscle Cells in Leiomyoma and Myometrium of Human Uterus after Gossypol Treatment, ACTA Academiae Medicinae Sinicae, 9:299-301 (1987).

Yu, Probing Into the Mechanism of Action, Metabolism and Toxicity of Gossypol by Studying its (+)- And (−)- Stereoisomers, Journal of Ethnopharmacology 20:65-78 (1987).

Zhang et al., The (+)-enantiomer of gossypol inhibits proliferation of stromal cells derived from human breast adipose tissues by enhancing transforming growth factor $a_1$ production, International Journal of Oncolocy 13:1291-1297 (1998).

Boyfield et al., "n-(substituted-phenyl)piperazines:" Bioorganic And Medicinal Chemistry Letters, 6:1227-32 (1996).

Rao, "Agents acting on the central nervous system. XIII:", Journal of Mecicinal Chemistry 13:516-22 (1970).

Singh et al., "Antihypertensive and cns depressent properties of 3-(gamma-p-fluorobenzoylpropyl)2,3,4,4a,5,6-hexahydro-a)h)-pyrazinol (1-2-a)quinoline hydrochloride", Experientia 29:1529-30 (1973).

Singh et al., "Pharmacological studies on 3[gamma-(p-fluorobenzoly)propyl]-2,3,4,4a,5,6, hexahydro-1-(H)pyrazinol(1,2,-a)quinoline hydrochlori (Compound 69/83)" Arrzneimittel Forschung Drug Research 28:1641-4 (1978).

Vichanova et al., Antibiotics (moscow) 13:828-829 (1968) (Abstract in English).

Becattini et al., Rational Design and Real Time, In-Cell Detection of the Proapoptotic Activity of a Novel Compound Targeting Bcl-XL: Chem Biol 11:389 (2004).

Brzezinski et al., Selective Esterification of Gossypol by Copper Acetate in Acetonitrile-Spectroscopi Studies; Spectroscopy Lett 27:1143 (1994).

Dowd et al., Crystal and Molecular Structure of an Enantiomeric Gossypol-Acetic Acid Clathrate; J am Oil Chem Soc 76:1343 (1999).

Dowd et al., A Correction to the Molecular Structure of Enantiomeric Gossypol; J Am Oil Chem Soc 78:1171 (2001).

Dowd et al., The Gossypol-Cyclododecanone (1/2) inclusion Complex; Acta Crystallogr C 59:397 (2003).

Dowd et al., The (−) -Gossypol-2,4-pentanedione (1:2) inclusion complex; J Chem Crystallogr 34:559 (2004).

Freedman et al., Determination of the Absolute Configuration and Solution Conformation of Gossypol by Vibrational Circular Dichroism; Chirality 15:196 (2003).

Gonzalez Correa et al., New Gossypol Derivatives; J Am Oil Chem Soc 43:678 (1966).

Han, X Y Jie He Za Zhi 2:159 (1982 (Chinese).

Hei et al., Electron Microscope Examination of Biopsy of Testis Tissue from the Patients with Tumors after Oral Treatment with Gossypol; Acta Acad Med Sinicae 61:527 (1981) (Chinese with Translation).

Jaroszewski et al., Effects of Gossypol on Drug-Sensitive and Drug-Resistant Cancer Cells; Proc Am Assoc Cancer Res 31:377 (1990).

Kable et al., Potency, Selectivity and Cell Cycle Dependence of Catechols in Human Tumor Cells In Vitro; Biochem Pharmacol 37:1171 (1988).

Kim et al., Gossypol, a Hyperthermic Sensitizer of HeLa Cells; Cancer Res 45:6338 (1985).

Liu et al., The (−)-Enantiomer of Gossypol Possesses Higher Anticancer Potency than Racemic Gossypol in Human Breast Cancer; Ancticancer Res 22:33 (2002).

McClarty et al., Ribonucleotide Reductase: A Intracellular Target for the Male Antifertility Agent, Gossypol; Biochem Biophys Res Commun 133:300 (1985).

Miller et al., Structure of Gossypol. IV. Anhydrogossypol and its Derivatives; J Am Chem Cos 59:1736 (1937).

Molla et al., Influence of 5-Hydroxytryptamine on the Combination Effect of Lonidamine or Gossypol and Hyperthermia on Ehrlich Tumour in Vivo;Anticancer Res 7:361 (1987).

Senzer, Hyperthermia: Chemotherapeutic and biologic response Modifications; Strahlenther Onkol 165:729 (1989).

Tripathy et al., Gossypol Effects on Breast Cancer Oncogene Expression and Membrane Receptor Signal Transduction; Breast Cancer Res Treat 16:160 (1990).

Vermel, The Search for Antitumor Substances of Plant Origin; Acta Unio Internationalis Contra Cancrum 20:211 (1964).

Vermel et al., Voprosy Oncologii 10:88 (1964) (Russian).

Xu, A Laboratory Investigation on the Antitumor Effects of Gossypol; Med J Jinan Univ 2:39 (1987) (Chinese with translation).

Zakhidov et al., Ezvestiia Akademii Nauk SSSR Seriia Biologicheskaia 4:694 (1994) (Russian).

Zhang et al., Comparison of the Killing Effect of Levorotatory, Dextrorotatory and Recemic Gossypol on HeLa Cells; Acta Acad Med Sinicae 7:384 (Chinese with translation).

Zhang et al., Analysis of the Possible Mechanism of the Cytotoxic Effect of Gossypol in Mice, Rats and Human Tumor Cell Lines; Acta Acad Med Sinicae 8:486 (1986) (Chinese with translation).

Zhang et al., In Vitro Antiproliferative Effect of Two New Platinum-Containing Bile Acid Derivatives:Bamet-U2 and Bamet-D3; Anticancer Res 18:4807 (1998).

Zhang et al., Differential Proliferative Responses to the (−)-enantiomer of Gossypol in Cultured Human Breast Epithelial and Stromal Cells; Proc Amer Assoc Cancer Res 40:4 (1999).

Wu et al., J. Chromatography 433:141 (1988).

Shen et al., Ch. J. Magnetic Resonance 20:373 (2003).

Meyers et al., Tetrahedron 54:10493 (1998).

Brzezinski et al., J. Mol. Structure 230:261 (1990).

Matlin et al., J. Liquid Chromatography 12:1485 (1989).

Jaroazewski et al., Chirality 4:216 (1992).

Przybylski et al., J. Mol. Structure 691:227 (2004).

Przybylski et al., J. Mol. Structure 654:167 (2003).

Przybylski et al., J. Mol Structure 569:147 (2001).

Haas et al., J. Org. Chem. 30:4111 (1965).

Przyblski et al., J. Mol. Structure 699:65 (2004).

Dao, Disssertation, University of Paris XI (2002).

U.S. Appl. No. 60/941,217, filed May 31, 2007, Holmlund.

U.S. Appl. No.: 10/806,088 - Office Communication Mailed Dec. 21, 2004.

U.S. Appl. No.: 10/806,088 - Office Communication Mailed Oct. 3, 2005.

U.S. Appl. No.: 10/806,088 - Office Communication Mailed May 1, 2006.

U.S. Appl. No.: 10/806,088 - Office Communication Mailed Aug. 4, 2006.

U.S. Appl. No.: 10/806,088 - Office Communication Mailed Jan. 16, 2007.

U.S. Appl. No.: 10/806,088 - Office Communication Mailed Mar. 19, 2007.

Gdaniec et al., Gossypol: Comprehensive Supramolecular Chemistry 6:117-200, 1999.

Jiang et al., "Inhibitory Action of Gossypol on the Growth of MAT-LyLu Prostate Cancer Cells is Associated with Stimulation of Transforming Growth Factor-a1 (TGF-a1)", Biology of Reproduction 60:252 (1999).

Jiang et al., "Differing Effects of Gossypol on MAT-LYLU Cells and MAT-LYLU Cells From Metastasized Lung of MAT=LYLU Cell-Bearing Copenhagen Rats," Society for the Study of Reproduction 58:89 (1999).

Koll et al., "A Phase I Study of Gossypol (GP) in HIV-Infected Patients (pts) in Mexico," Abstracts of the 33rd ICAC 245:687 (1993).

Reidenberg, "Studies of gossypol in the treatment of cancer", Reproductive Medicine, 305-308 (1999).

Willemsen, An Oxazoline-Based Approach to the Total Asymmetric Synthesis of (S)-Gossypol, UMI PROQuest Digital Dissertations - Full Citation & Abstract (1998).

US 7,432,300 B2

GOSSYPOL CO-CRYSTALS AND THE USE THEREOF

This application is a Divisional of U.S. patent application Ser. No. 11/089,096, filed Mar. 24, 2005, now U.S. Pat. No. 7,342,046 which claims priority to U.S. Provisional Application 60/556,249 filed Mar. 25, 2004, each of which are herein incorporated by reference in their entireties.

BACKGROUND OF THE INVENTION

1. Field of the Invention

This invention is in the field of medicinal chemistry. In particular, the invention relates to compositions comprising co-crystals of (−)-gossypol with a $C_{1-8}$ carboxylic acid or $C_{1-8}$ sulfonic acid which are useful as inhibitors of Bcl-2 family proteins. The invention also relates to the use of co-crystals of (−)-gossypol with a $C_{1-8}$ carboxylic acid or $C_{1-8}$ sulfonic acid for inducing apoptosis in cells and for sensitizing cells to the induction of apoptotic cell death.

2. Related Art

The aggressive cancer cell phenotype is the result of a variety of genetic and epigenetic alterations leading to deregulation of intracellular signaling pathways (Ponder, Nature 411:336 (2001)). The commonality for all cancer cells, however, is their failure to execute an apoptotic program, and lack of appropriate apoptosis due to defects in the normal apoptosis machinery is a hallmark of cancer (Lowe et al., Carcinogenesis 21:485 (2000)). Most of the current cancer therapies, including chemotherapeutic agents, radiation, and immunotherapy, work by indirectly inducing apoptosis in cancer cells. The inability of cancer cells to execute an apoptotic program due to defects in the normal apoptotic machinery is thus often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., Carcinogenesis 21:485 (2000); Nicholson, Nature 407: 810 (2000)). Accordingly, current and future efforts towards designing and developing new molecular target-specific anti-cancer therapies to improve survival and quality of life of cancer patients must include strategies that specifically target cancer cell resistance to apoptosis. In this regard, targeting crucial negative regulators that play a central role in directly inhibiting apoptosis in cancer cells represents a highly promising therapeutic strategy for new anticancer drug design.

Two classes of central negative regulators of apoptosis have been identified. The first class of regulators is the inhibitor of apoptosis proteins (IAPs) (Deveraux et al., Genes Dev. 13:239 (1999); Salvesen et al., Nat. Rev. Mol. Cell. Biol. 3:401 (2002)). IAP proteins potently suppress apoptosis induced by a large variety of apoptotic stimuli, including chemotherapeutic agents, radiation, and immunotherapy in cancer cells.

The second class of central negative regulators of apoptosis is the Bcl-2 family of proteins (Adams et al., Science 281: 1322 (1998); Reed, Adv. Pharmacol. 41:501 (1997); Reed et al., J. Cell. Biochem. 60:23 (1996)). Bcl-2 is the founding member of the family and was first isolated as the product of an oncogene. The Bcl-2 family now includes both anti-apoptotic molecules such as Bcl-2 and Bcl-$X_L$ and pro-apoptotic molecules such as Bax, Bak, Bid, and Bad. Bcl-2 and Bcl-$X_L$ are overexpressed in many types of human cancer (e.g., breast, prostate, colorectal, lung, etc.), including Non-Hodgkin's lymphoma, which is caused by a chromosomal translocation (t14, 18) that leads to overexpression of Bcl-2. This suggests that many cancer cell types depend on the elevated levels of Bcl-2 and/or Bcl-$X_L$ to survive the other cellular derangements that simultaneously both define them as cancerous or pre-cancerous cells and cause them to attempt to execute the apoptosis pathway. Also, increased expression of Bcl-2 family proteins has been recognized as a basis for the development of resistance to cancer therapeutic drugs and radiation that act in various ways to induce cell death in tumor cells.

Bcl-2 and Bcl-$X_L$ are thought to play a role in tumor cell migration and invasion, and therefore, metastasis. Amberger et al., Cancer Res. 58:149 (1998); Wick et al., FEBS Lett, 440:419 (1998); Mohanam et al., Cancer Res. 53:4143 (1993); Pedersen et al, Cancer Res., 53:5158 (1993). Bcl-2 family proteins appear to provide tumor cells with a mechanism for surviving in new and non-permissive environments (e.g., metastatic sites), and contribute to the organospecific pattern of clinical metastatic cancer spread. Rubio, Lab Invest. 81:725 (2001); Fernández et al., Cell Death Differ. 7:350 (2000)). Anti-apoptotic proteins such as Bcl-2 and/or Bcl-$X_L$ are also thought to regulate cell-cell interactions, for example through regulation of cell surface integrins. Reed, Nature 387:773 (1997); Frisch et al., Curr. Opin. Cell Biol. 9:701 (1997); Del Bufalo et al., FASEB J. 11:947 (1997).

Therapeutic strategies for targeting Bcl-2 and Bcl-$X_L$ in cancer to restore cancer cell sensitivity and overcome resistance of cancer cells to apoptosis have been extensively reviewed (Adams et al., Science 281:1322 (1998); Reed, Adv. Pharmacol. 41:501 (1997); Reed et al., J. Cell. Biochem. 60:23 (1996)). Currently, Bcl-2 antisense therapy is in several Phase III clinical trials for the treatment of solid and non-solid tumors.

Gossypol is a naturally occurring double biphenolic compound derived from crude cotton seed oil (Gossypium sp.). Human trials of gossypol as a male contraceptive have demonstrated the safety of long term administration of these compounds (Wu, Drugs 38:333 (1989)). Gossypol has more recently been shown to have some anti-proliferative effects (Flack et al., J. Clin. Endocrinol. Metab. 76:1019 (1993); Bushunow et al., J. Neuro-Oncol. 43:79, (1999); Van Poznak et al., Breast Cancer Res. Treat. 66:239 (2001)). (−)-Gossypol and its derivatives recently have been shown to be potent inhibitors of Bcl-2 and Bcl-$X_L$ and to have strong anti-cancer activity (U.S. Patent Application No. 2003/0008924).

A composition comprising racemic gossypol and acetic acid is known in the art (Sigma-Aldrich Corp., St. Louis, Mo.). Previous attempts to crystallize (−)-gossypol have resulted in crystals that are too poor for X-ray analysis (Gdaniec et al., "Gossypol," in Comprehensive Supramolecular Chemistry (Atwood et al. eds.), Vol. 6, Pergamon) or in co-crystals of (−)-gossypol and acetone when using a solution of racemic gossypol acetic acid in acetone (Dowd et al., J. Am. Oil Chem. Soc. 76:1343 (1999)).

SUMMARY OF THE INVENTION

The present invention relates to compositions comprising co-crystals of (−)-gossypol (formula I) with a $C_{1-8}$ carboxylic acid or $C_{1-8}$ sulfonic acid ("(−)-gossypol co-crystals"). These compositions are useful for inhibiting the activity of anti-apoptotic Bcl-2 family proteins, inducing apoptosis in cells, and increasing the sensitivity of cells to inducers of apoptosis.

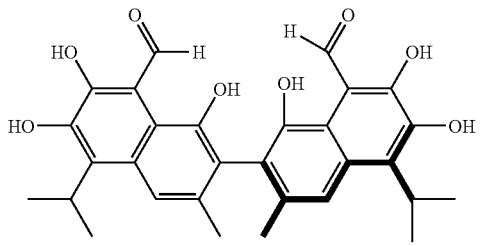

It is generally accepted that the inability of cancer cells or their supporting cells to undergo apoptosis in response to genetic lesions or exposure to inducers of apoptosis (such as anticancer agents and radiation) is a major factor in the onset and progression of cancer. The induction of apoptosis in cancer cells or their supporting cells (e.g., neovascular cells in the tumor vasculature) is thought to be a universal mechanism of action for virtually all of the effective cancer therapeutic drugs or radiation therapies on the market or in practice today. One reason for the inability of a cell to undergo apoptosis is increased expression and accumulation of anti-apoptotic Bcl-2 family proteins.

The present invention contemplates that exposure of animals suffering from cancer to therapeutically effective amounts of (−)-gossypol co-crystal that inhibit the function(s) of anti-apoptotic Bcl-2 family proteins will kill cancer cells or supporting cells outright (those cells whose continued survival is dependent on the overactivity of Bcl-2 family proteins) and/or render such cells as a population more susceptible to the cell death-inducing activity of cancer therapeutic drugs or radiation therapies. The present invention contemplates that (−)-gossypol co-crystals will satisfy an unmet need for the treatment of multiple cancer types, either when administered as monotherapy to induce apoptosis in cancer cells dependent on anti-apoptotic Bcl-2 family proteins function, or when administered in a temporal relationship with other cell death-inducing cancer therapeutic drugs or radiation therapies so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, it is expected that combination treatment of animals with a therapeutically effective amount of a composition of the present invention and a course of an anticancer agent or radiation will produce a greater tumor response and clinical benefit in such animals compared to those treated with the composition or anticancer drugs/radiation alone. Put another way, because the compositions lower the apoptotic threshold of all cells that express anti-apoptotic Bcl-2 family proteins, the proportion of cells that successfully execute the apoptosis program in response to the apoptosis inducing activity of anticancer drugs/radiation will be increased. Alternatively, the compositions of the present invention are expected to allow administration of a lower, and therefore less toxic and more tolerable, dose of an anticancer agent and/or radiation to produce the same tumor response/clinical benefit as the conventional dose of the anticancer agent/radiation alone. Since the doses for all approved anticancer drugs and radiation treatments are known, the present invention contemplates combination therapies with various combinations of known drugs/treatments with the present compositions. Also, since the compositions of the present invention act at least in part by inhibiting anti-apoptotic Bcl-2 family proteins, the exposure of cancer cells and supporting cells to therapeutically effective amounts of the compositions can be temporally linked to coincide with the attempts of cells to execute the apoptosis program in response to the anticancer agent or radiation therapy. Thus, in some embodiments, administering the compositions of the present invention in connection with certain temporal relationships, will provide especially efficacious therapeutic practices.

(−)-Gossypol co-crystal is useful for the treatment, amelioration, or prevention of disorders responsive to induction of apoptotic cell death, e.g., disorders characterized by dysregulation of apoptosis, including hyperproliferative diseases such as cancer. In certain embodiments, (−)-gossypol co-crystal can be used to treat, ameliorate, or prevent cancer that is characterized by resistance to cancer therapies (e.g., those which are chemoresistant, radiation resistant, hormone resistant, and the like). In additional embodiments, (−)-gossypol co-crystal can be used to treat, ameliorate, or prevent metastatic cancer. In other embodiments, (−)-gossypol co-crystal can be used to treat hyperproliferative diseases characterized by overexpression of anti-apoptotic Bcl-2 family proteins.

The present invention provides methods of treating a viral, microbial, or parasitic infection in an animal, comprising administering to said animal a therapeutically effective amount of (−)-gossypol co-crystal.

The present invention provides pharmaceutical compositions comprising (−)-gossypol co-crystal and a pharmaceutically acceptable carrier.

The invention further provides methods of making a pharmaceutical composition comprising admixing (−)-gossypol co-crystal in a therapeutically effective amount to induce apoptosis in cells or to sensitize cells to inducers of apoptosis with a pharmaceutically acceptable carrier The invention further provides kits comprising (−)-gossypol co-crystal and instructions for administering the composition to an animal. The kits may optionally contain other therapeutic agents, e.g., anticancer agents.

The invention also provides methods of making (−)-gossypol co-crystal. For example, co-crystals may be prepared by a method comprising dissolving (−)-gossypol in acetone to form a solution, filtering the solution, adding a $C_{1-8}$ carboxylic acid or $C_{1-8}$ sulfonic acid into the solution with mixing until the solution turns turbid, leaving the turbid solution at room temperature then at a reduced temperature to form co-crystals, collecting the co-crystals, washing the co-crystals with a solvent, and drying the co-crystals.

BRIEF DESCRIPTION OF THE DRAWINGS/FIGURES

DETAILED DESCRIPTION OF THE INVENTION

Figure 1:
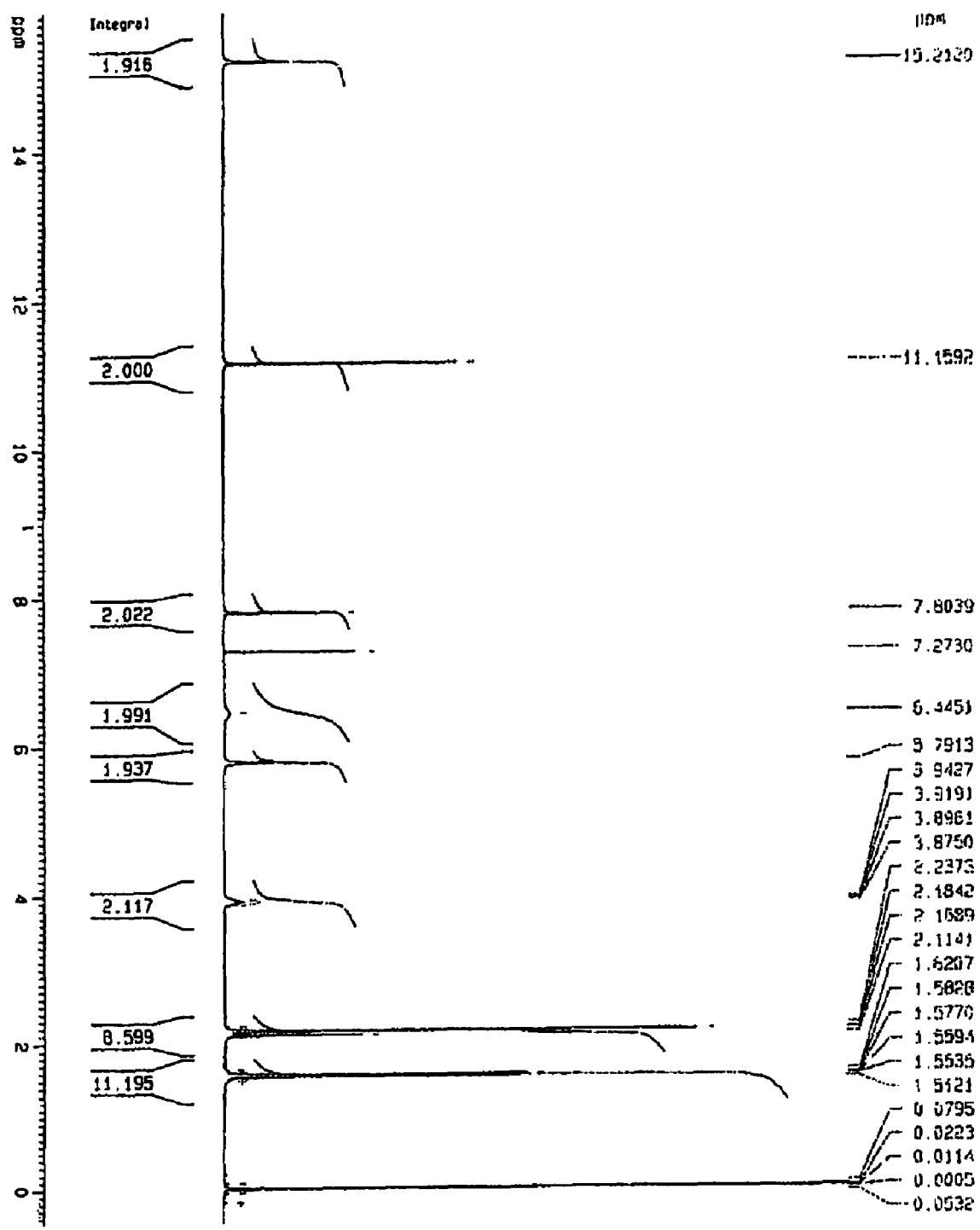
FIG. 1 shows the $^1$H NMR spectrum of (−)-gossypol acetic acid co-crystal.

The present invention relates to compositions comprising co-crystals of (−)-gossypol with a $C_{1-8}$ carboxylic acid or $C_{1-8}$ sulfonic acid ("(−)-gossypol co-crystals"), which are useful as inhibitors of anti-apoptotic Bcl-2 family proteins. By inhibiting anti-apoptotic Bcl-2 family proteins, the (−)-gossypol sensitizes cells to inducers of apoptosis and, in some instances, itself induces apoptosis. Therefore, the invention relates to methods of sensitizing cells to inducers of apoptosis and to methods of inducing apoptosis in cells, comprising administering (−)-gossypol co-crystal alone or in combination with an inducer of apoptosis. The invention further relates to methods of treating, ameliorating, or preventing disorders in an animal that are responsive to induction of apoptosis comprising administering to the animal (−)-gossypol co-crystal and an inducer of apoptosis. Such disorders include those characterized by a dysregulation of apoptosis and those characterized by overexpression of anti-apoptotic Bcl-2 family proteins.

The terms "(−)-gossypol," or "(−)-gossypol compound/composition," as used herein, refer to an optically active composition of gossypol wherein the active molecules comprising the composition rotate plane polarized light counterclockwise (e.g., levorotatory molecules) as measured by a polarimeter. Preferably, the (−)-gossypol compound has an enantiomeric excess of 1% to 100%. In one embodiment, the (−)-gossypol compound has an enantiomeric excess of at least 10%, 20%, 30%, 40%, 50%, 60%, 70%, 80%, 90%, 91%, 92%, 93%, 94%, 95%, 96%, 97%, 98%, 99%, or 100% (−)-gossypol. In one example of a "(−)-gossypol compound", the specific rotation ($[\alpha]_D$) of the compound is about −350° to about −390°, about −375° to about −390°, or about −385° to about −390°. (See e.g., Dowd, Chirality, 15:486 (2003); Ciesielska et al., Chem. Phys. Lett. 353:69 (2992); Freedman et al., Chirality, 15:196 (2003); and Zhou et al., Kexue Tongbao, 28:1574 (1983)). Methods for resolving racemic gossypol compounds into substantially purified (+)- or (−)-gossypol are known (See e.g., Zhou et al., Kexue Tongbao, 28:1574 (1983) (wherein: L-phenylalanine methyl ester was mixed with the aldehyde groups of gossypol to form a Schiff's base with two diastereoisomers which were then resolved on a normal silica flash chromatography column. The filtrate was concentrated, and the residue was purified by chromatography on silica gel eluting with hexanes:EtOAc=3:1 to give two fractions. Acid hydrolysis of the two fractions in 5N HCl:THF (1:5, room temperature, overnight) regenerated the individual gossypol enantiomers, respectively. The first fraction with a higher $R_f$ value contained (−)-gossypol, and the second fraction with a lower $R_f$ value contained (+)-gossypol. The crude gossypol fractions were extracted into ether from the residue after removing THF from the reaction mixture. The gossypol fractions were then purified by chromatography on silica gel and eluted with hexanes:EtOAc (3:1 ratio) to give optically pure gossypol, with a yield of 30-40% in two steps. The optical rotatory dispersion values for these products were $\alpha_D$=−352° (c=0.65, CHCl$_3$) for (−)-gossypol, and $\alpha_D$=+341° (c=0.53, CHCl$_3$)).

The term "$C_{1-8}$ carboxylic acid," as used herein, refers to straight-chained or branched, aromatic or non-aromatic, saturated or unsaturated, substituted or unsubstituted $C_{1-8}$ carboxylic acid, including, but not limited to, formic acid, acetic acid, propionic acid, n-butyric acid, t-butyric acid, n-pentanoic acid, 2-pentanoic acid, n-hexanoic acid, 2-hexanoic acid, n-heptanoic acid, n-octanoic acid, acrylic acid, succinic acid, fumaric acid, malic acid, tartaric acid, citric acid, lactic acid, and benzoic acid.

The term "$C_{1-8}$ sulfonic acid," as used herein, refers to straight-chained or branched, aromatic or non-aromatic, saturated or unsaturated, substituted or unsubstituted $C_{1-8}$ sulfonic acid, including, but not limited to, methanesulfonic acid, ethanesulfonic acid, n-propanesulfonic acid, 2-propanesulfonic acid, n-butanesulfonic acid, n-pentanesulfonic acid n-hexanesulfonic acid, n-heptanesulfonic acid, n-octanesulfonic acid, and benzenesulfonic acid.

The term "(−)-gossypol co-crystal," as used herein, refers to a composition comprising co-crystals of (−)-gossypol and a $C_{1-8}$ carboxylic acid or $C_{1-8}$ sulfonic acid.

The term "Bcl-2 family proteins," as used herein, refers to both the anti-apoptotic members of the Bcl-2 family, including, but not limited to, Bcl-2, Bcl-XL, Mcl-1, A1/BFL-1, BOO-DIVA, Bcl-w, Bcl-6, Bcl-8, and Bcl-y, and the pro-apoptotic members of the Bcl-2 family, including, but not limited to, Bak, Bax, Bad, tBid, Hrk, Bim, Bmf, as well as other Bcl-2 homology domain 3 (BH3) containing proteins that are regulated by gossypol compounds.

The term "overexpression of anti-apoptotic Bcl-2 family proteins," as used herein, refers to an elevated level (e.g., aberrant level) of mRNAs encoding for an anti-apoptotic Bcl-2 family protein(s), and/or to elevated levels of anti-apoptotic Bcl-2 family protein(s) in cells as compared to similar corresponding non-pathological cells expressing basal levels of mRNAs encoding anti-apoptotic Bcl-2 family proteins or having basal levels of anti-apoptotic Bcl-2 family proteins. Methods for detecting the levels of mRNAs encoding anti-apoptotic Bcl-2 family proteins or levels of anti-apoptotic Bcl-2 family proteins in a cell include, but are not limited to, Western blotting using anti-apoptotic Bcl-2 family protein antibodies, immunohistochemical methods, and methods of nucleic acid amplification or direct RNA detection. As important as the absolute level of anti-apoptotic Bcl-2 family proteins in cells is to determining that they overexpress anti-apoptotic Bcl-2 family proteins, so also is the relative level of anti-apoptotic Bcl-2 family proteins to other pro-apoptotic signaling molecules (e.g., pro-apoptotic Bcl-2 family proteins) within such cells. When the balance of these two are such that, were it not for the levels of the anti-apoptotic Bcl-2 family proteins, the pro-apoptotic signaling molecules would be sufficient to cause the cells to execute the apoptosis program and die, said cells would be dependent on the anti-apoptotic Bcl-2 family proteins for their survival. In such cells, exposure to an inhibiting effective amount of an anti-apoptotic Bcl-2 family protein inhibitor will be sufficient to cause the cells to execute the apoptosis program and die. Thus, the term "overexpression of an anti-apoptotic Bcl-2 family protein" also refers to cells that, due to the relative levels of pro-apoptotic signals and anti-apoptotic signals, undergo apoptosis in response to inhibiting effective amounts of compounds that inhibit the function of anti-apoptotic Bcl-2 family proteins.

The terms "anticancer agent" and "anticancer drug," as used herein, refer to any therapeutic agent (e.g., chemotherapeutic compounds and/or molecular therapeutic compounds), radiation therapies, or surgical interventions, used in the treatment of hyperproliferative diseases such as cancer (e.g., in mammals).

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g. a compound of Formula I), an animal or a cell within an animal more susceptible, or more responsive, to the biological effects (e.g., promotion or retardation of an aspect of cellular function including, but not limited to, cell growth, proliferation, invasion, angiogenesis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least 10%, at least 20%, at least 30%, at least 40%, at least 50%, at least 60%, at least 70%, at least 80%, at least 90%, at least 100%, at least 150%, at least 200%, at least 350%, at least 300%, at least 350%, at least 400%, at least 450%, or at least 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, including for example, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "synergistic," as used herein, refers to an effect obtained when (−)-gossypol co-crystal and a second agent are administered together (e.g., at the same time or one after the other) that is greater than the additive effect of (−)-gossypol co-crystal and the second agent when administered individually. The synergistic effect allows for lower doses of (−)-gossypol co-crystal and/or the second agent to be administered or provides greater efficacy at the same doses. The synergistic effect obtained can be at least 10%, at least 20%, at least 30%, at least 40%, at least 50%, at least 60%, at least 70%, at least 80%, at least 90%, at least 100%, at least 125%, at least 0.150%, at least 175%, at least 200%, at least 250%, at least 300%, at least 350%, at least 400%, or at least 500% more than the additive effect of the (−)-gossypol co-crystal compound and the second agent when administered individually. For example, with respect to the treatment of cancer, the synergistic effect can be a decrease in the rate of tumor growth, a decrease in tumor mass, a decrease in the number of metastases, an increase in time to tumor progression, or an increase in survival time. The co-administration of (−)-gossypol co-crystal and an anticancer agent may allow for the use of lower doses of (−)-gossypol co-crystal and/or the anticancer agent such that the cancer is effectively treated while avoiding any substantial toxicity to the subject.

The term "about," as used herein, includes the recited number+/−10%. Thus, "about 0.5" means 0.45 to 0.55.

The inhibitors of anti-apoptotic Bcl-2 family proteins of the present invention are compositions comprising co-crystals of (−)-gossypol with a $C_{1-8}$ carboxylic acid or $C_{1-8}$ sulfonic acid ("(−)-gossypol co-crystals"). (−)-Gossypol co-crystal is expected to be more stable than (−)-gossypol alone. Those skilled in the art will appreciate the importance of compound stability in the manufacturing, storage, shipping, and/or handling of pharmaceutical compositions. The present compositions are expected to be more stable than previously described compositions comprising (−)-gossypol. Any $C_{1-8}$ carboxylic acid or $C_{1-8}$ sulfonic acid that is capable of stabilizing (−)-gossypol can be used in the invention. The molar ratio of (−)-gossypol to carboxylic acid or sulfonic acid in (−)-gossypol co-crystal ranges from about 10:1 to about 1:10, preferably about 2:1 to about 1:2, more preferably about 1:1. In some embodiments, the molar ratio of (−)-gossypol to carboxylic acid or sulfonic acid in (−)-gossypol co-crystal can be about 10:1, 9:1, 8:1, 7:1, 6:1, 5:1, 4:1, 3:1, 2:1, 1.5:1, 1:1, 1:1.5, 1:2, 1:3, 1:4, 1:5, 1:6, 1:7, 1:8, 1:9, or 1:10.

In one embodiment of the invention the $C_{1-8}$ carboxylic acid is acetic acid. In another embodiment, (−)-gossypol co-crystal comprises (−)-gossypol and acetic acid in a molar ratio of about 1:1. In a preferred embodiment, the 1:1 co-crystal of (−)-gossypol and acetic acid is in the form of yellow or pale yellow needle-shaped crystals. In another preferred embodiment, the co-crystal is characterized by integration of $^1$H NMR spectrum at δ 2.11 (s, 3H) which is one methyl signal of acetic acid and δ 2.18 (s, 6H) which is two methyl signals of gossypol.

The compositions of this invention may be prepared using methods known to those of skill in the art and as disclosed in the Examples. In one embodiment, co-crystals are prepared by dissolving (−)-gossypol in acetone to form a solution, filtering the solution, adding a $C_{1-8}$ carboxylic acid or $C_{1-8}$ sulfonic acid into the solution with mixing until the solution turns turbid, leaving the turbid solution at room temperature and then at reduced temperature to form co-crystals, collecting the co-crystals, washing the co-crystals with a solvent, and drying the co-crystals. In one embodiment, the solution is mixed by constant stirring. Reduced temperature is less than about 20° C., preferably about 0-15° C., more preferably about 4° C. The time for co-crystal formation may range from 1 hour to 1 day; preferably the time is about 14 hours. The co-crystals may be collected by any suitable means, including by filtration. The solvent for washing the co-crystals may be any suitable solvent, e.g., hexane, pentane, benzene, toluene, or petroleum ether. The washed co-crystals may be dried at room temperature, preferably in a lightproof container. The co-crystals may also be dried in a vacuum drier, preferably at an elevated temperature (e.g., about 30-60° C., more preferably about 40° C.) for about 6-72 hours, preferably about 12-48 hours.

(−)-Gossypol has been shown to bind to Bcl-2 and Bcl-$X_L$ at the BH3 binding groove and to have significant anticancer activity (U.S. Patent Application No. 2003/0008924). An important aspect of the present invention is that (−)-gossypol co-crystal binds to and inhibits anti-apoptotic Bcl-2 proteins in the same manner as gossypol. However, (−)-gossypol co-crystal is expected to be more stable than (−)-gossypol. Moreover, (−)-gossypol is a more potent inhibitor than racemic gossypol. Thus, compositions comprising (−)-gossypol co-crystal may be used to induce apoptosis and also potentiate the induction of apoptosis in response to apoptosis induction signals. It is contemplated that these compositions sensitize cells to inducers of apoptosis, including cells that are resistant to such inducers. The compositions of the present invention can be used to induce apoptosis in any disorder that can be treated, ameliorated, or prevented by the induction of apoptosis. Thus, the present invention provides compositions and methods for targeting animals characterized as overexpressing an anti-apoptotic Bcl-2 family protein. In some of the embodiments, the cells (e.g., cancer cells) show elevated expression levels of one or more anti-apoptotic Bcl-2 family proteins as compared to non-pathological samples (e.g., non-cancerous cells). In other embodiments, the cells operationally manifest elevated expression levels of anti-apoptotic Bcl-2 family proteins by virtue of executing the apoptosis program and dying in response to administration of an inhibiting effective amount of (−)-gossypol co-crystal, said response occurring, at least in part, due to the dependence in such cells on anti-apoptotic Bcl-2 family protein function for their survival.

In some embodiments, the compositions and methods of the present invention are used to treat diseased cells, tissues, organs, or pathological conditions and/or disease states in an animal (e.g., a mammalian subject including, but not limited to, humans and veterinary animals). In this regard, various diseases and pathologies are amenable to treatment or prophylaxis using the present methods and compositions. A non-limiting exemplary list of these diseases and conditions includes, but is not limited to, cancers such as breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like; T and B cell mediated autoimmune diseases, inflammatory diseases, infections, hyperproliferative diseases, AIDS, degenerative conditions, vascular diseases, and the like. In some embodiments, the cancer cells being treated are metastatic. In other embodiments, the cancer cells being treated are resistant to anticancer agents.

In some embodiments, infections suitable for treatment with the compositions and methods of the present invention include, but are not limited to, infections caused by viruses, bacteria, fungi, parasites, mycoplasma, prions, and the like.

Some embodiments of the present invention provide methods for administering an effective amount of (−)-gossypol co-crystal and at least one additional therapeutic agent (including, but not limited to, chemotherapeutic agents, antineoplastic agents, antimicrobial agents, antiviral agents, antifungal agents, and anti-inflammatory agents) and/or therapeutic technique (e.g., surgical intervention, and/or radiotherapies). In some embodiments, the combination of (−)-gossypol co-crystal and one or more therapeutic agents will have a greater effect as compared to the administration of either compound alone. In other embodiments, the combination of (−)-gossypol co-crystal and one or more therapeutic agents is expected to result in a synergistic effect (i.e., more than additive) as compared to the administration of either one alone.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In preferred embodiments, anticancer agents comprise agents that induce or stimulate apoptosis. Agents that induce apoptosis include, but are not limited to, radiation (e.g., X-rays, gamma rays, UV); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, BEXXAR, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine, dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide (−)-gossypol co-crystal and at least one anti-hyperproliferative or antineoplastic agent; e.g., selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil), floxuridine (fluorode-oxyuridine), and cytarabine (cytosine arabinoside)); and 3) purine analogs (e.g., mercaptopurine (6-mercaptopurine), thioguanine (6-thioguanine), and pentostatin (2'-deoxycofommycin)).

In still further embodiments, chemotherapeutic agents suitable for use in the compositions and methods of the present invention include, but are not limited to: 1) vinca alkaloids (e.g., vinblastine, vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin and carboplatin); 7) anthracenediones (e.g., mitoxantrone); 8) substituted ureas (e.g., hydroxyurea); 9) methylhydrazine derivatives (e.g., procarbazine (N-methylhydrazine)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) anti-androgens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4H-pyrazolo[3,4-d]pyrimidin-4-one monosodium salt) | Zyloprim | GlaxoSmithKline, Research Triangle Park, NC |
| Altretamine (N,N,N',N',N'',N'',-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |

TABLE 1-continued

| | | |
|---|---|---|
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-a-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12- | Adriamycin, Rubex | Pharmacia & Upjohn Company |

TABLE 1-continued

| Drug | Brand | Company |
|---|---|---|
| naphthacenedione hydrochloride) | | |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-,3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$•($C_2H_4O_2$)$_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate | Gleevec | Novartis AG, Basel, |

TABLE 1-continued

| | | |
|---|---|---|
| (4-[(4-Methyl-1-piperazinyl)methyl]-N-[4-methyl-3-[[4-(3-pyridinyl)-2-pyrimidinyl]amino]-phenyl]benzamide methanesulfonate) | | Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino) carbonyloxy]-1H-pyrano[3',4':6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)—N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl | Neulasta | Amgen, Inc |

TABLE 1-continued

| | | |
|---|---|---|
| human G-CSF (Filgrastim) and monomethoxypolyethylene glycol) | | |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7]indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |

TABLE 1-continued

| | | |
|---|---|---|
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R—(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Preferred conventional anticancer agents for use in administration with the present compounds include, but are not limited to, adriamycin, 5-fluorouracil, etoposide, camptothecin, actinomycin D, mitomycin C, cisplatin, docetaxel, gemcitabine, carboplatin, oxaliplatin, bortezomib, gefitinib, and bevacizumab. These agents can be prepared and used singularly, in combined therapeutic compositions, in kits, or in combination with immunotherapeutic agents, and the like.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" ninth edition, Eds. Hardman et al., 1996.

The present invention provides methods for administering (−)-gossypol co-crystal with radiation therapy. The invention is not limited by the types, amounts, or delivery and administration systems used to deliver the therapeutic dose of radiation to an animal. For example, the animal may receive photon radiotherapy, particle beam radiation therapy, radioisotope therapy (e.g., radioconjugates with monoclonal antibodies), other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by patients. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to a patient, so long as the dose of radiation is tolerated by the patient without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. The dose of radiation is preferably fractionated for maximal target cell exposure and reduced toxicity.

The total dose of radiation administered to an animal preferably is about 0.01 Gray (Gy) to about 100 Gy. More preferably, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), preferably 1-2 Gy (e.g., 1.5-2 Gy). The daily dose of radiation should be sufficient to induce destruction of the targeted cells. If stretched over a period, radiation preferably is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. Preferably, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the present invention, (−)-gossypol co-crystal and one or more therapeutic agents or anticancer agents are administered to an animal under one or more of the following conditions: at different periodicities, at different durations, at different concentrations, by different administration routes, etc. In some embodiments, (−)-gossypol co-crystal is administered prior to the therapeutic or anticancer agent, e.g., 0.5, 1, 2 3, 4, 5, 10, 12, or 18 hours, 1, 2, 3, 4, 5, or 6 days, 1, 2, 3, or 4 weeks prior to the administration of the therapeutic or anticancer agent. In some embodiments, (−)-gossypol co-crystal is administered after the therapeutic or anticancer agent, e.g., 0.5, 1, 2 3, 4, 5, 10, 12, or 18 hours, 1, 2, 3, 4, 5, or 6 days, 1, 2, 3, or 4 weeks after the administration of the anticancer agent. In some embodiments, (−)-gossypol co-crystal and the therapeutic or anticancer agent are administered concurrently but on different schedules, e.g., (−)-gossypol co-crystal is administered daily while the therapeutic or anticancer agent is administered once a week, once every two weeks, once every three weeks, or once every four weeks. In other embodiments, (−)-gossypol co-crystal is administered once a week while the therapeutic or anticancer agent is administered daily, once a week, once every two weeks, once every three weeks, or once every four weeks.

Pharmaceutical compositions can be produced by combining (−)-gossypol co-crystal in a therapeutically effective amount to induce apoptosis in cells or to sensitize cells to inducers of apoptosis with a pharmaceutically acceptable carrier. The novel pharmaceutical compositions of the present invention comprise intact (−)-gossypol co-crystal. In some embodiments, the pharmaceutical compositions comprise (−)-gossypol co-crystal in combination with a liquid in which the co-crystal is substantially insoluble (e.g., water) such that a suspension is formed.

Compositions within the scope of this invention include all compositions wherein the compositions of the present invention are contained in an amount which is effective to achieve its intended purpose. While individual needs vary, determination of optimal ranges of effective amounts of each component is within the skill of the art. Typically, the compositions may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. Preferably, about 0.01 to about 10 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, and most preferably, from about 0.01 to about 5 mg/kg.

The unit oral dose may comprise from about 0.01 to about 200 mg, preferably about 0.1 to about 100 mg of the composition. The unit dose may be administered one or more times daily as one or more tablets or capsules each containing from about 0.1 to about 100 mg, conveniently about 0.25 to 50 mg of the composition.

In a topical formulation, the composition may be present at a concentration of about 0.01 to 100 mg per gram of carrier. In a preferred embodiment, the composition is present at a concentration of about 0.07-1.0 mg/ml, more preferably, about 0.1-0.5 mg/ml, most preferably, about 0.4 mg/ml.

In addition to administering (−)-gossypol co-crystal as a raw chemical, the compositions of the invention may be administered as part of a pharmaceutical preparation containing suitable pharmaceutically acceptable carriers comprising excipients and auxiliaries which facilitate processing of the compositions into preparations which can be used pharmaceutically. Preferably, the preparations, particularly those preparations which can be administered orally or topically and which can be used for the preferred type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by injection, topically or orally, contain from about 0.01 to 99 percent, preferably from about 0.25 to 75 percent of active compound(s), together with the excipient.

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like).

The compositions and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal, or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Creams are preferably formulated from a mixture of mineral oil, self-emulsifying beeswax and water in which mixture the active ingredient, dissolved in a small amount of an oil such as almond oil, is admixed. A typical example of such a cream is one which includes about 40 parts water, about 20 parts beeswax, about 40 parts mineral oil and about 1 part almond oil.

Ointments may be formulated by mixing a suspension of the active ingredient in a vegetable oil such as almond oil with warm soft paraffin and allowing the mixture to cool. A typical example of such an ointment is one which includes about 30% almond oil and about 70% white soft paraffin by weight.

Lotions may be conveniently prepared by preparing a suspension of the active ingredient in a suitable high molecular weight alcohol such as propylene glycol or polyethylene glycol.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

Preparation of (−)-Gossypol Acetic Acid Co-Crystal

All chemicals and reagents were purchased from Aldrich Chemical Co. or Lancaster Synthesis Inc. and used without further purification. (−)-Gossypol (1 g) was dissolved in acetone (6 ml) and filtered. Acetic acid was added into the constantly stirred filtrate until the solution turned turbid. The mixture was left at room temperature for 2 hours and then at 4° C. for 2 hours. The co-crystals were collected by filtration using a Buchner funnel under reduced pressure and washed with a small amount of hexane. Pure (−)-gossypol acetic acid was first dried in a lightproof container and further dried in a vacuum drier at 40° C. for 24 hours.

EXAMPLE 2

Characterization of (−)-Gossypol Acetic Acid Co-Crystals (−)-Gossypol acetic acid co-crystals were yellow or pale yellow and needle shaped. The co-crystals were readily soluble in acetone and ether, slightly soluble in chloroform and ethanol, and sparsely soluble in petroleum. The co-crystals were insoluble in water. The uncorrected melting point of the co-crystals was determined to be 178-180° C. using a Mel-Temp apparatus.

Figure 2:
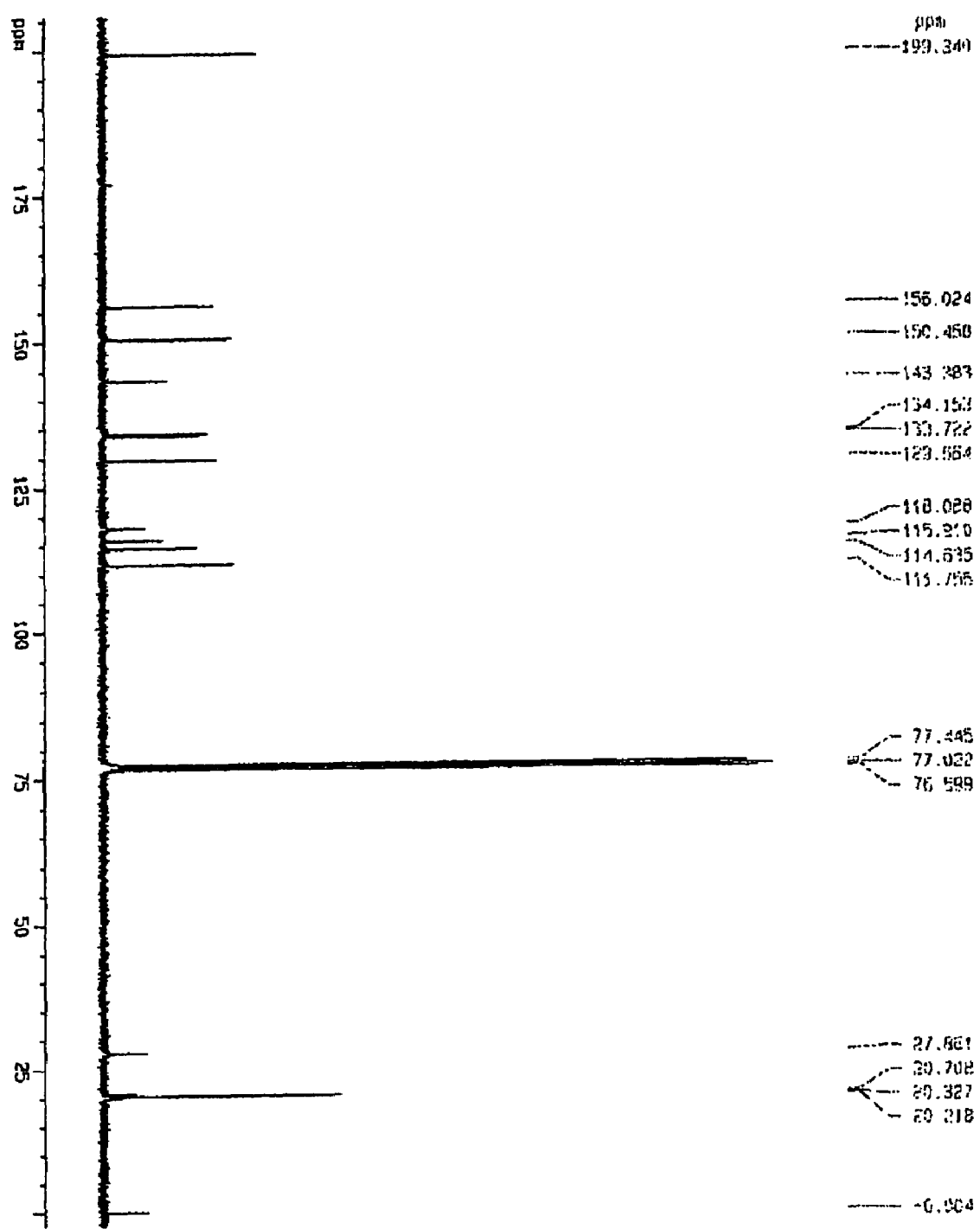
FIG. 2 shows the $^{13}$C NMR spectrum of (−)-gossypol acetic acid co-crystal.

[1]H and $^{13}$C nuclear magnetic resonance (NMR) spectra of the co-crystals (FIGS. 1 and 2) were recorded on a Bruker 300 instrument. Samples were dissolved in an appropriate deuterated solvent ($CDCl_3$). Proton chemical shifts were reported as parts per million (δ) relative to tetramethylsilane (0.00 ppm), which was used as an internal standard. Chemical shifts for $^{13}$C NMR spectra were reported as δ relative to deuterated chloroform ($CDCl_3$, 77.0 ppm). $^1$H NMR (300 MHz, $CDCl_3$) δ 15.21 (s, 2H), 11.16 (s, 2H), 7.80 (s, 2H), 6.45 (s, 2H), 5.79 (s, 2H), 4.08-3.80 (m, 2H), 2.18 (s, 6H), 2.11 (s, 3H), 1.58 (d, J=6.8 Hz, 12H). $^{13}$C NMR (75 MHz, $CDCl_3$) δ 199.4, 176.8, 156.0, 150.5, 143.4, 134.1, 133.7, 129.7, 118.1, 115.9, 114.6, 111.8, 27.9, 20.7, 20.3, 20.2. Based on the $^1$H NMR spectrum, the co-crystal was determined to be a complex of (−)-gossypol with acetic acid at a molar ratio of 1:1.

Figure 3:
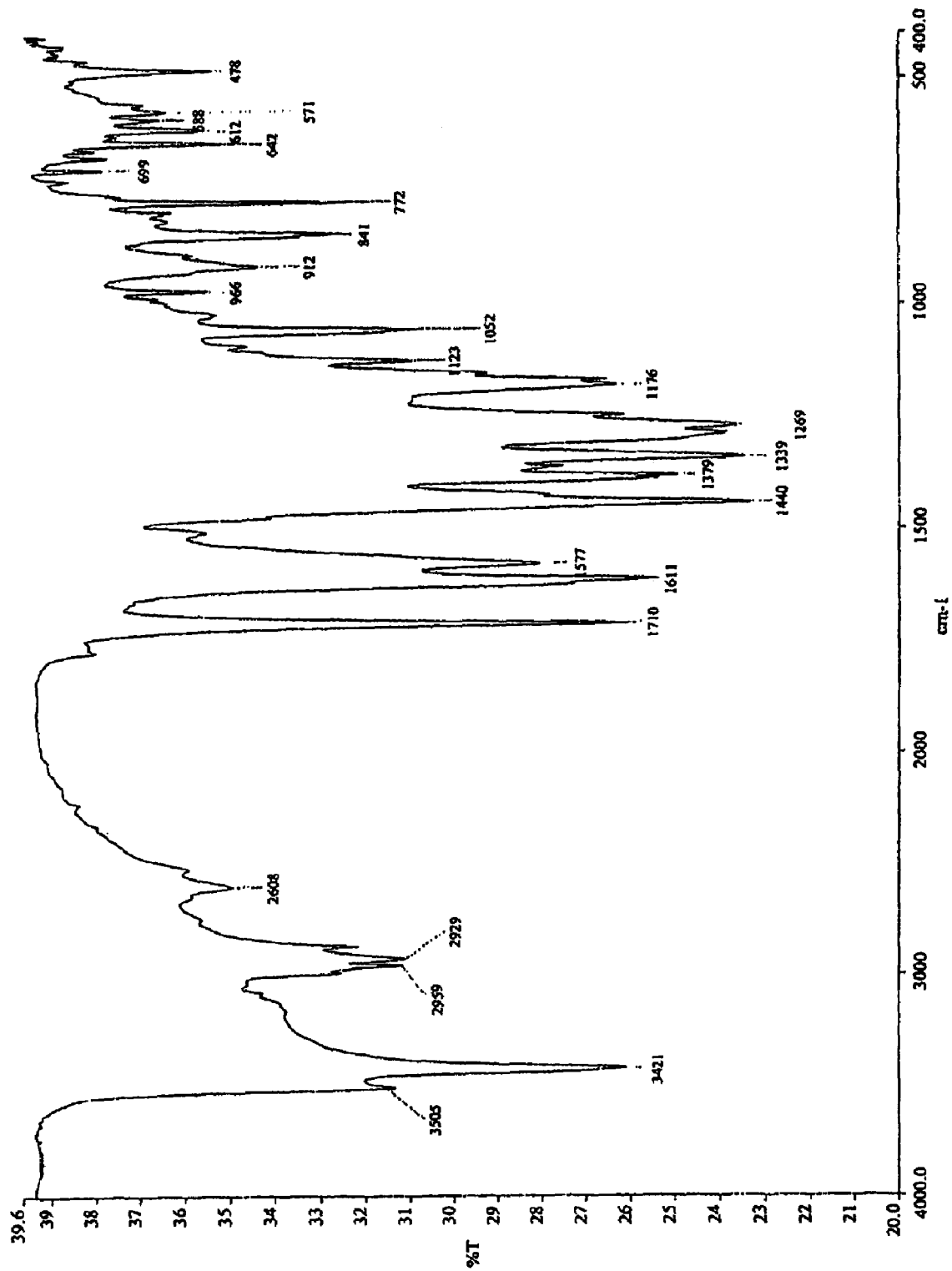
FIG. 3 shows the infrared spectrum of (−)-gossypol acetic acid co-crystal.

The infrared spectrum (FIG. 3) of the co-crystals was recorded on a Perkin-Elmer FT-IR spectrometer. IR(KBr) 3421, 2959, 2929, 1710, 1611, 1577, 1440, 1379, 1339, 1269, 1176, 1052, 841, 772 $cm^{-1}$.

Figure 4:
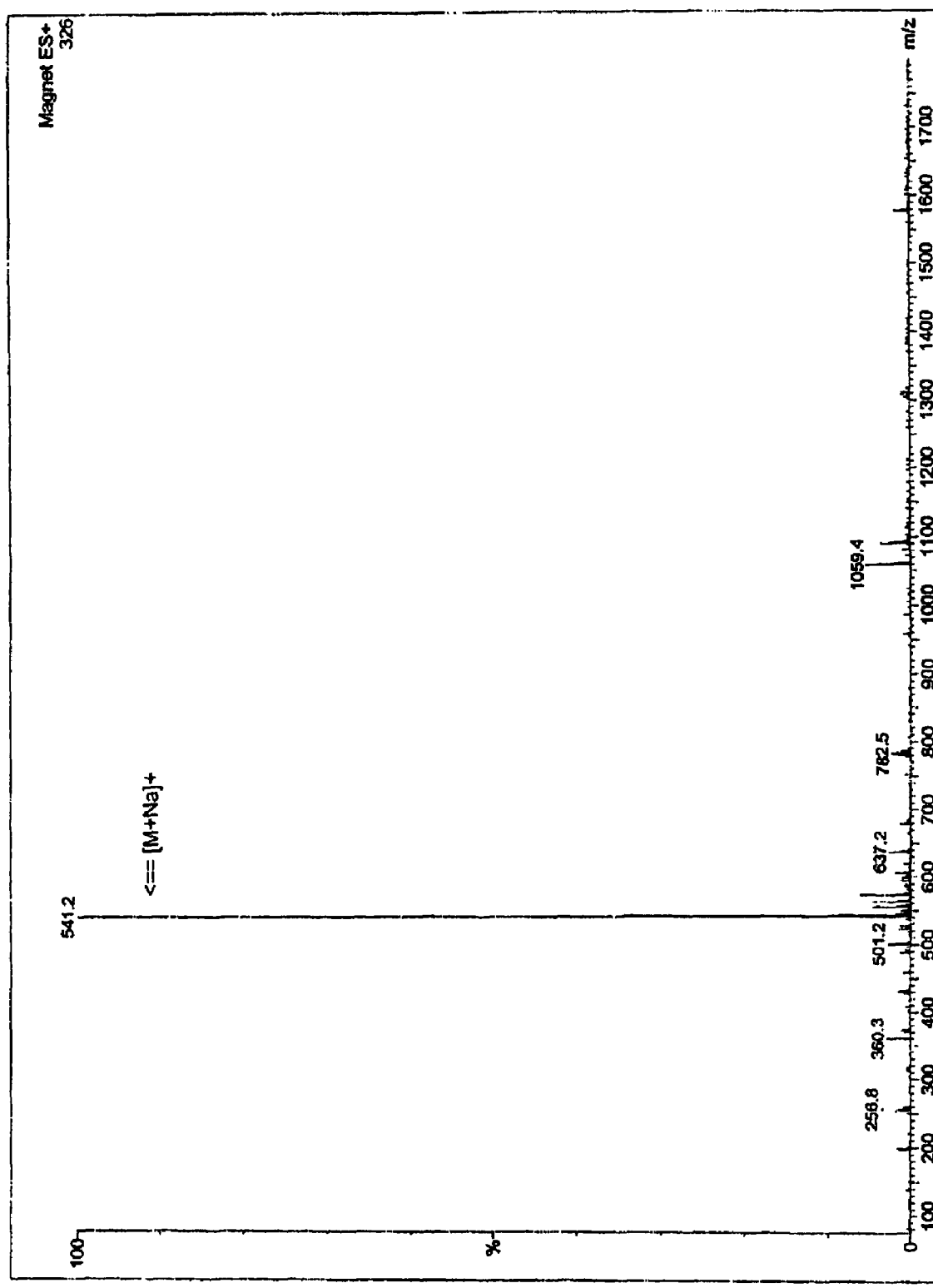
FIG. 4 shows the mass spectrum of (−)-gossypol acetic acid co-crystal.

The electrospray mass spectrum (FIG. 4) of the co-crystals was performed on a Micromass AutoSpec Ultima Magnetic sector mass spectrometer. MS m/z 541 $(M+Na)^+$.

Figure 5:
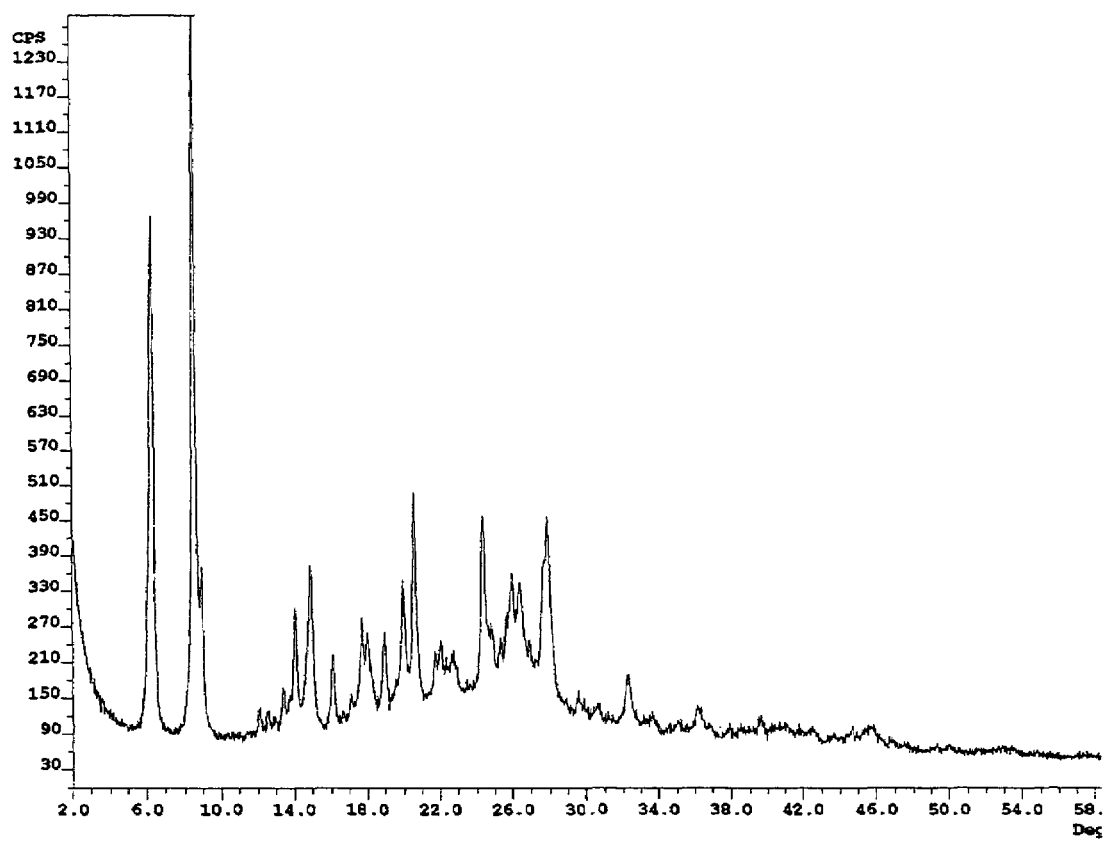
FIG. 5 shows the X-ray powder diffraction spectrum of (−)-gossypol acetic acid co-crystal.

The X-ray powder diffraction spectrum (FIG. 5) of the co-crystals was recorded on a Scintag X-ray powder diffractometer. Based on the spectrum, the co-crystal was determined to be a complex of (−)-gossypol with acetic acid at a molar ratio of 1:1.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

What is claimed is:

1. A method of treating a hyperproliferative disease or cancer in an animal, comprising administering to said animal a therapeutically effective amount of a pharmaceutical composition comprising co-crystals of (−)-gossypol with acetic acid in a molar ratio of about 1:1 and a pharmaceutically acceptable carrier.

2. The method of claim 1, further comprising administering to said animal an inducer of apoptosis.

3. The method of claim 2, wherein said inducer of apoptosis is a chemotherapeutic agent.

4. The method of claim 2, wherein said inducer of apoptosis is radiation.

5. The method of claim 2, wherein said composition is administered prior to said inducer of apoptosis.

6. The method of claim 2, wherein said composition is administered concurrently with said inducer of apoptosis.

7. The method of claim 2, wherein said composition is administered after said inducer of apoptosis.

8. A method of treating a viral, microbial, or parasitic infection in an animal, comprising administering to said animal a therapeutically effective amount of a pharmaceutical composition comprising co-crystals of (−)-gossypol with acetic acid in a molar ratio of about 1:1 and a pharmaceutically acceptable carrier.

9. A method of treating, ameliorating, or preventing a disorder responsive to the induction of apoptosis in an animal, comprising administering to said animal a therapeutically effective amount of a pharmaceutical composition comprising co-crystals of (−)-gossypol with acetic acid in a molar ratio of about 1:1 and a pharmaceutically acceptable carrier.

10. The method of claim 9, further comprising administering to said animal an inducer of apoptosis.

* * * * *

UNITED STATES PATENT AND TRADEMARK OFFICE
CERTIFICATE OF CORRECTION

PATENT NO. : 7,432,300 B2
APPLICATION NO. : 11/818766
DATED : October 7, 2008
INVENTOR(S) : Shaomeng Wang et al.

It is certified that error appears in the above-identified patent and that said Letters Patent is hereby corrected as shown below:

Title Page at (75) Inventors, the second named inventor "Jiangyong Chen" should read --Jianyong Chen--.

Signed and Sealed this

Second Day of February, 2010

David J. Kappos
*Director of the United States Patent and Trademark Office*